US011952635B2

(12) United States Patent
Blanck et al.

(10) Patent No.: US 11,952,635 B2
(45) Date of Patent: Apr. 9, 2024

(54) BIOMARKERS OF LOW GRADE GLIOMA AND PEDIATRIC NEUROBLASTOMA

(71) Applicant: University of South Florida, Tampa, FL (US)

(72) Inventors: George Blanck, Tampa, FL (US); Saif Zaman, Ocala, FL (US); Boris Il'ich Chobrutskiy, Tampa, FL (US)

(73) Assignee: University of South Florida, Tampa, FL (US)

( * ) Notice: Subject to any disclaimer, the term of this patent is extended or adjusted under 35 U.S.C. 154(b) by 162 days.

(21) Appl. No.: 17/697,294

(22) Filed: Mar. 17, 2022

(65) Prior Publication Data

US 2022/0205052 A1    Jun. 30, 2022

Related U.S. Application Data

(62) Division of application No. 16/580,644, filed on Sep. 24, 2019, now Pat. No. 11,279,981.

(60) Provisional application No. 62/735,230, filed on Sep. 24, 2018.

(51) Int. Cl.
*C12Q 1/6886* (2018.01)
*A61K 31/7076* (2006.01)

(52) U.S. Cl.
CPC ........ *C12Q 1/6886* (2013.01); *A61K 31/7076* (2013.01); *C12Q 2600/112* (2013.01); *C12Q 2600/154* (2013.01); *C12Q 2600/158* (2013.01)

(58) Field of Classification Search
CPC ............ C12Q 1/6886; C12Q 2600/112; C12Q 2600/154; C12Q 2600/158; A61K 31/7076
USPC .......................................................... 514/46
See application file for complete search history.

(56) References Cited

U.S. PATENT DOCUMENTS

| | | | |
|---|---|---|---|
| 5,550,111 A | 8/1996 | Suhadolnik | |
| 6,949,521 B2 | 9/2005 | Chu et al. | |
| 8,143,313 B2 | 3/2012 | Kubow et al. | |
| 2011/0027797 A1 | 2/2011 | Somasundram et al. | |
| 2011/0251086 A1* | 10/2011 | Vandesompele | C12Q 1/6883 435/6.12 |
| 2011/0256547 A1 | 10/2011 | Somasundram et al. | |
| 2014/0322354 A1 | 10/2014 | Goel et al. | |

OTHER PUBLICATIONS

Yoon et al. The Anticancer Properties of Cordycepin and Their Underlying Mechanisms. Int. J. Mol. Sci. 2018, 19, 3027. (Year: 2018).*
Song et al. Isatin inhibits proliferation and induces apoptosis of SH-SY5Y neuroblastoma cells in vitro and in vivo. European Journal of Pharmacology 702 (2013) 235-241. (Year: 2013).*
Abel et al. Imbalance of the mitochondrial pro- and anti-apoptotic mediators in neuroblastoma tumours with unfavourable biology. European Journal of Cancer 41 (2005) 635-646. (Year: 2005).*
Chaicharoenaudomrung et al. Cordycepin induces apoptotic cell death of human brain cancer through the modulation of autophagy. Toxicology in Vitro 46 (2018) 113-121. Available online Oct. 4, 2017. (Year: 2018).*
Akinrinmade, Olusiji A., et al. "Human MAP tau based targeted cytolytic fusion proteins." Biomedicines 5.3 (2017): 36.
Arai, Tetsuaki, et al. "Distinct isoforms of tau aggregated in neurons and glial cells in brains of patients with Pick's disease, corticobasal degeneration and progressive supranuclear palsy." Acta neuropathologica 101.2 (2001): 167-173.
Arnal, Isabelle, and Richard H. Wade. "How does taxol stabilize microtubules?" Current biology 5.8 (1995): 900-908.
Bai, Y-H., et al., "A Novel Tumor-Suppressor, CDH18, Inhibits Glioma Cell Invasiveness Via UQCRC2 and Correlates with the Prognosis of Glioma Patients," Cellular Physiology and Biochemistry, vol. 48, 2018, pp. 1755-1770.
Borroni, Barbara, et al. "Mutation within TARDBP leads to frontotemporal dementia without motor neuron disease." Human mutation 30.11 (2009): E974-E983.
Bougé, Anne-Laure, and Marie-Laure Parmentier. "Tau excess impairs mitosis and kinesin-5 function, leading to aneuploidy and cell death." Disease models & mechanisms 9.3 (2016): 307-319.
Brodeur, Garrett M., et al. "Amplification of N-myc in untreated human neuroblastomas correlates with advanced disease stage." Science 224.4653 (1984): 1121-1124.
Buée, Luc, et al. "From tau phosphorylation to tau aggregation: what about neuronal death?" Biochem Soc Trans. (2010): 967-972.
Cheng, Judy M., et al. "Preferential amplification of the paternal allele of the n-myc gene in human neuroblastomas." Nature genetics 4.2 (1993): 191.
Choi, Sunghyun, et al. "Protective effect of tat PTD-Hsp27 fusion protein on tau hyperphosphorylation induced by okadaic acid in the human neuroblastoma cell line SH-SY5Y." Cellular and molecular neurobiology 35.7 (2015): 1049-1059.
Claus, Elizabeth B., et al. "Survival and low-grade glioma: the emergence of genetic information." Neurosurgical focus 38.1 (2015): E6.
Cohn, Susan L., et al. "The International Neuroblastoma Risk Group (INRG) classification system: an INRG task force report." Journal of clinical oncology 27.2 (2009): 289.
Colodner, Kenneth J., and Mel B. Feany. "Glial fibrillary tangles and JAK/STAT-mediated glial and neuronal cell death in a *Drosophila* model of glial tauopathy." Journal of Neuroscience 30.48 (2010): 16102-16113.
Davidoff AM. "Neuroblastoma." Semin Pediatr Surg 2012; 21:2-14.
Emanuel, Beverly S., et al. "N-myc amplification in multiple homogeneously staining regions in two human neuroblastomas." Proceedings of the National Academy of Sciences 82.11 (1985): 3736-3740.

(Continued)

*Primary Examiner* — Yih-Horng Shiao
(74) *Attorney, Agent, or Firm* — Meunier Carlin & Curfman LLC

(57) ABSTRACT

The present disclosure relates to biomarkers and methods for determining or predicting survival of patients with low grade glioma (LGG) or pediatric neuroblastoma. Further disclosed are methods of diagnosing and treating patients with low grade glioma (LGG) or pediatric neuroblastoma.

9 Claims, 15 Drawing Sheets

(56) References Cited

OTHER PUBLICATIONS

Ferrer, Isidre, et al. "Glial and neuronal tau pathology in tauopathies: characterization of disease-specific phenotypes and tau pathology progression." Journal of Neuropathology & Experimental Neurology 73.1 (2014): 81-97.
Floris, Gianluca, et al. "Clinical phenotypes and radiological findings in frontotemporal dementia related to TARDBP mutations." Journal of neurology 262.2 (2015): 375-384.
Ford, Shea A., and George Blanck. "Signal persistence and amplification in cancer development and possible, related opportunities for novel therapies." Biochimica et Biophysica Acta (BBA)-Reviews on Cancer 1855.1 (2015): 18-23.
Frost, Bess, Jürgen Götz, and Mel B. Feany. "Connecting the dots between tau dysfunction and neurodegeneration." Trends in cell biology 25.1 (2015): 46-53.
Galvan, Veronica, et al. "Caspase cleavage of members of the amyloid precursor family of proteins." Journal of neurochemistry 82.2 (2002): 283-294.
Gao, Jianjiong, et al. "Integrative analysis of complex cancer genomics and clinical profiles using the cBioPortal." Sci. Signal. 6.269 (2013): p. l1-p. l1.
Gervais, François G., et al. "Involvement of caspases in proteolytic cleavage of Alzheimer's amyloid-β precursor protein and amyloidogenic Aβ peptide formation." Cell 97.3 (1999): 395-406.
Grossman, Robert L., et al. "Toward a shared vision for cancer genomic data." New England Journal of Medicine 375.12 (2016): 1109-1112.
Harada, A., et al. "Altered microtubule organization in small-calibre axons of mice lacking tau protein." Nature 369.6480 (1994): 488.
Harms, Matthew M., Timothy M. Miller, and Robert H. Baloh. "TARDBP-related amyotrophic lateral sclerosis." GeneReviews® [Internet]. University of Washington, Seattle, 2015.
Hartmann, Christian, et al. "Molecular markers in low-grade gliomas: predictive or prognostic?" Clinical Cancer Research 17.13 (2011): 4588-4599.
Hueng, Dueng-Yuan, et al. "Cordycepin inhibits migration of human glioblastoma cells by affecting lysosomal degradation and protein phosphatase activation." The Journal of nutritional biochemistry 41 (2017): 109-116.
Iijima-Ando, Kanae, et al. "A DNA damage-activated checkpoint kinase phosphorylates tau and enhances tau-induced neurodegeneration." Human molecular genetics 19.10 (2010): 1930-1938.
Ikeda, Hirokuni, et al. "The estrogen receptor influences microtubule-associated protein tau (MAPT) expression and the selective estrogen receptor inhibitor fulvestrant downregulates MAPT and increases the sensitivity to taxane in breast cancer cells." Breast Cancer Research 12.3 (2010): R43.
Ikeda, K., et al. "Glial tau pathology in neurodegenerative diseases: their nature and comparison with neuronal tangles." Neurobiology of aging 19.1 (1998): S85-S91.
Jazvinšćak Jembrek, Maja, Patrick R. Hof, and Goran Šimić. "Ceramides in Alzheimer's disease: key mediators of neuronal apoptosis induced by oxidative stress and Aβ accumulation." Oxidative medicine and cellular longevity 2015 (2015): 346783.
Kanehisa, Minoru. "Use of statistical criteria for screening potential homologies in nucleic acid sequences." (1984): 203-213.
Kawaguchi, Atsushi, et al. "Identification and validation of a gene expression signature that predicts outcome in malignant glioma patients." International journal of oncology 40.3 (2012): 721-730.
Kellogg, Ryan A., and Savaş Tay. "Noise facilitates transcriptional control under dynamic inputs." Cell 160.3 (2015): 381-392.
Khurana, Vikram, et al. "A neuroprotective role for the DNA damage checkpoint in tauopathy." Aging cell 11.2 (2012): 360-362.
Koo, Dong-Hoe, et al. "Tau and PTEN status as predictive markers for response to trastuzumab and paclitaxel in patients with HER2-positive breast cancer." Tumor Biology 36.8 (2015): 5865-5871.
Kruman, Inna I., et al. "Cell cycle activation linked to neuronal cell death initiated by DNA damage." Neuron 41.4 (2004): 549-561.

Lee, Moonhee, Edith McGeer, and Patrick L. McGeer. "Activated human microglia stimulate neuroblastoma cells to upregulate production of beta amyloid protein and tau: implications for Alzheimer's disease pathogenesis." Neurobiology of aging 36.1 (2015): 42-52.
Lee, Young Ju, et al. "Selenium treatment significantly inhibits tumor necrosis factor-α-induced cell death and tau hyperphosphorylation in neuroblastoma cells." Molecular medicine reports 10.4 (2014): 1869-1874.
Li, Zhi-hua, et al. "Tau proteins expressions in advanced breast cancer and its significance in taxane-containing neoadjuvant chemotherapy." Medical oncology 30.3 (2013): 591.
Louis, Chrystal U., and Jason M. Shohet. "Neuroblastoma: molecular pathogenesis and therapy." Annual review of medicine 66 (2015): 49-63.
Mandelkow, Eckhard, and Eva-Maria Mandelkow. "Microtubules and microtubule-associated proteins." Current opinion in cell biology 7.1 (1995): 72-81.
Maris JM, Hogarty MD, Bagatell R, Cohn SL. "Neuroblastoma" Lancet 2007; 369:2106-20.
Mauro, James A., and George Blanck. "Functionally distinct gene classes as bigger or smaller transcription factor traps: a possible stochastic component to sequential gene expression programs in cancer." Gene 536.2 (2014): 398-406.
Mielke, Michelle M., et al. "Cerebrospinal fluid sphingolipids, B-amyloid, and tau in adults at risk for Alzheimer's disease." Neurobiology of aging 35.11 (2014): 2486-2494.
Monroy-Ramirez, Hugo C., et al. "Alterations in the nuclear architecture produced by the overexpression of tau protein in neuroblastoma cells." Journal of Alzheimer's Disease 36.3 (2013): 503-520.
Nishimura, Masaki, et al. "Immunocytochemical characterization of glial fibrillary tangles in Alzheimer's disease brain." The American journal of pathology 146.5 (1995): 1052.
Petroni, Daniel, et al. "Low-dose methylmercury-induced oxidative stress, cytotoxicity, and tau-hyperphosphorylation in human neuroblastoma (SH-SY5Y) cells." Environmental toxicology 27.9 (2012): 549-555.
Ping, Zheng, et al. "Mining genome sequencing data to identify the genomic features linked to breast cancer histopathology." Journal of pathology informatics 5 (2014).
Russo, Roberta, et al. "Kinome expression profiling of human neuroblastoma tumors identifies potential drug targets for ultra high-risk patients." Carcinogenesis 38.10 (2017): 1011-1020.
Saarinen-Pihkala, Ulla M., et al. "Ultrahigh-risk group within the high-risk neuroblastoma category." Journal of pediatric hematology/oncology 35.6 (2013): e254-e259.
Samadi, Nasser, et al. "Lysophosphatidate induces chemoresistance by releasing breast cancer cells from taxol-induced mitotic arrest." PloS one 6.5 (2011): e20608.
Schiff, Peter B., Jane Fant, and Susan B. Horwitz. "Promotion of microtubule assembly in vitro by taxol." Nature 277.5698 (1979): 665.
Shen, X.-G., et al., "Downregulation of caspase-9 is a frequent event in patients with stage II colorectal cancer and correlates with poor clinical outcome," Colorectal Disease, vol. 12, No. 12, 2009, pp. 1213-1218.
Siegel, Rebecca L., Kimberly D. Miller, and Ahmedin Jemal. "Cancer statistics, 2016." CA: a cancer journal for clinicians 66.1 (2016): 7-30.
Sikaria, Dhiraj, et al. "Identification of specific feed-forward apoptosis mechanisms and associated higher survival rates for low grade glioma and lung squamous cell carcinoma." Journal of cancer research and clinical oncology 144.3 (2018): 459-468.
Silva, Aderbal RT, et al. "Repair of oxidative DNA damage, cell-cycle regulation and neuronal death may influence the clinical manifestation of Alzheimer's disease." PloS one 9.6 (2014): e99897.
Simpson, Julie E., et al. "A neuronal DNA damage response is detected at the earliest stages of A lzheimer's neuropathology and correlates with cognitive impairment in the M edical R esearch C ouncil's C ognitive F unction and A geing S tudy ageing brain cohort." Neuropathology and applied neurobiology 41.4 (2015): 483-496.

(56) References Cited

OTHER PUBLICATIONS

Snyder, James P., et al. "The binding conformation of Taxol in β-tubulin: a model based on electron crystallographic density." Proceedings of the National Academy of Sciences 98.9 (2001): 5312-5316.

Spillantini, Maria Grazia, and Michel Goedert. "Tau pathology and neurodegeneration." The Lancet Neurology 12.6 (2013): 609-622.

Wang, Kun, et al. "Tau expression correlated with breast cancer sensitivity to taxanes-based neoadjuvant chemotherapy." Tumor Biology 34.1 (2013): 33-38.

Wiernik, Peter H., et al. "Phase I clinical and pharmacokinetic study of taxol." Cancer research 47.9 (1987): 2486-2493.

Wu, J. M., A. M. DiPietrantonio, and T-C. Hsieh. "Mechanism of fenretinide (4-HPR)-induced cell death." Apoptosis 6.5 (2001): 377-388.

Yoon, So Young, Soo Jung Park, and Yoon Jung Park. "The anticancer properties of cordycepin and their underlying mechanisms." International journal of molecular sciences 19.10 (2018): 3027.

Zage, P.E., et al., "UBE4B Levels are Correlated With Clinical Outcomes in Neuroblastoma Patients and With Altered Neuroblastoma Cell Proliferation and Sensitivity to Epidermal Growth Factor Receptor Inhibitors," Cancer, vol. 119, No. 4, 2013 (epub 2012), pp. 915-923.

Zaman, Saif, Boris I. Chobrutskiy, and George Blanck. "MAPT (Tau) expression is a biomarker for an increased rate of survival in pediatric neuroblastoma." Cell Cycle 17.21-22 (2018): 2474-2483.

Zaman, Saif, et al. "MAPT (Tau) expression is a biomarker for an increased rate of survival for low-grade glioma." Oncology Reports 41.2 (2019): 1359-1366.

Zhou, Jie, et al. "Predictive value of microtubule-associated protein Tau in patients with recurrent and metastatic breast cancer treated with taxane-containing palliative chemotherapy." Tumor Biology 36.5 (2015): 3941-3947.

International Search Report and the Written Opinion issued for Application No. PCT/US2019/052691, dated Dec. 16, 2019.

Partial Supplementary European Search Report, dated Jun. 10, 2022, received in connection with corresponding EP Patent Application No. 19865417.0.

* cited by examiner

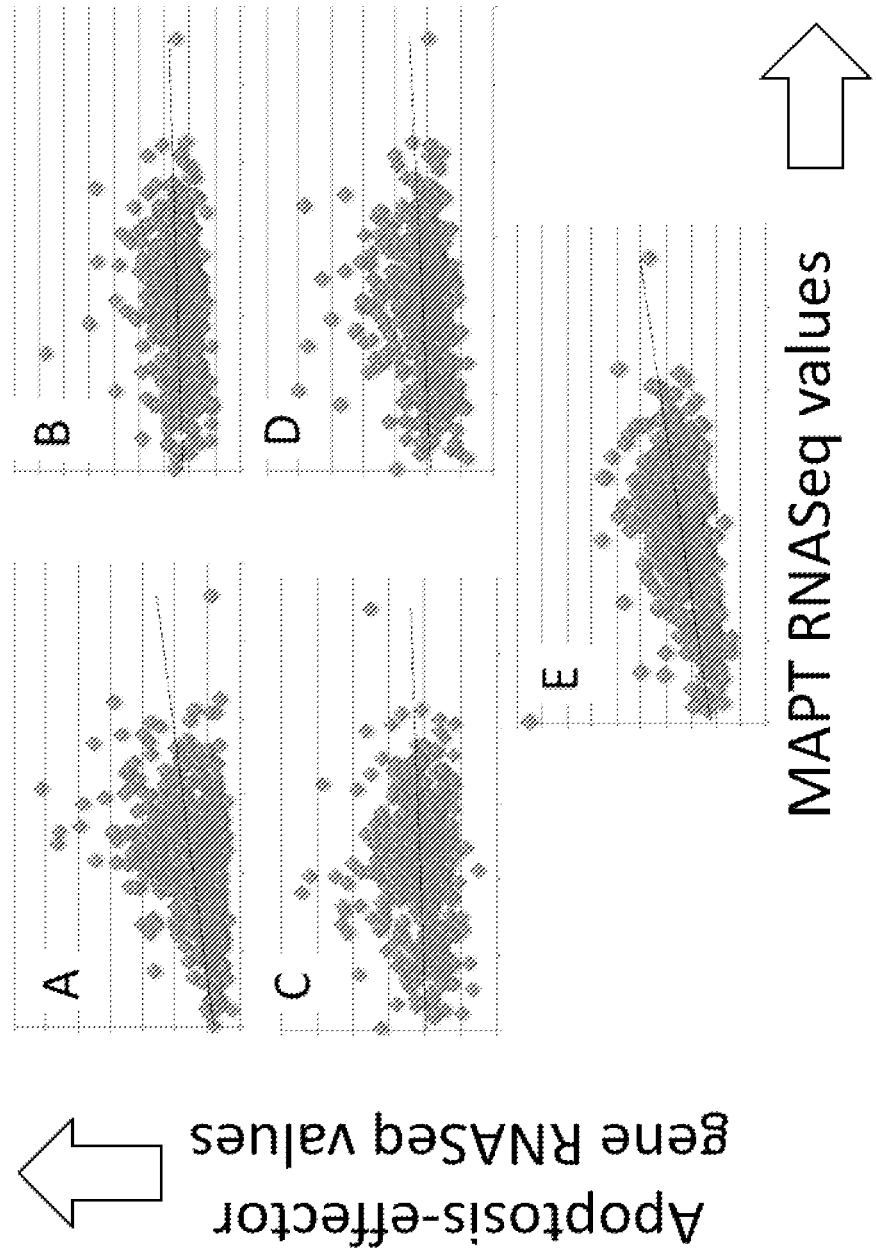
FIG. 3A, FIG. 3B, FIG. 3C, FIG. 3D, and FIG. 3E

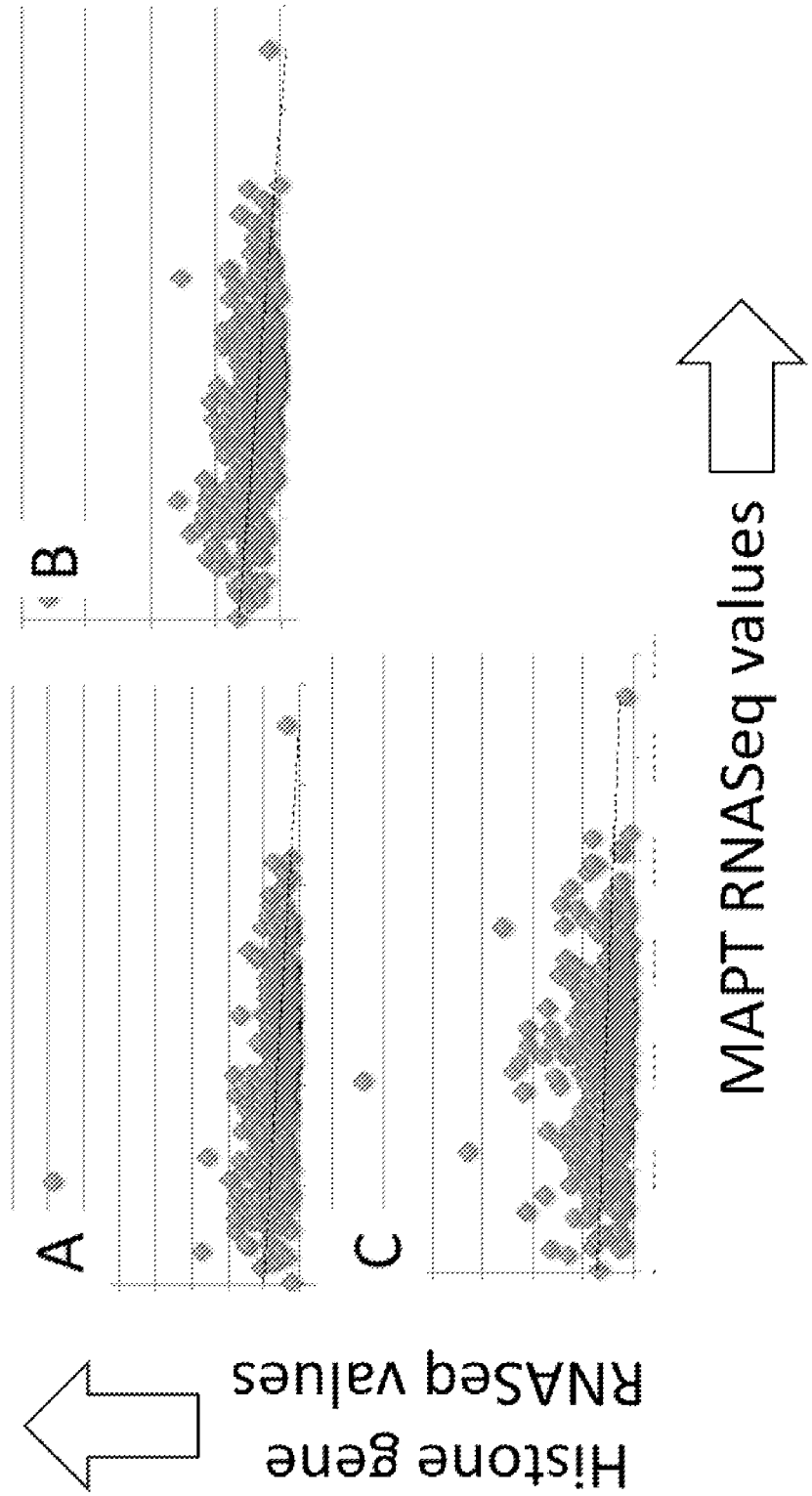
FIG. 5A, FIG. 5B, and FIG. 5C

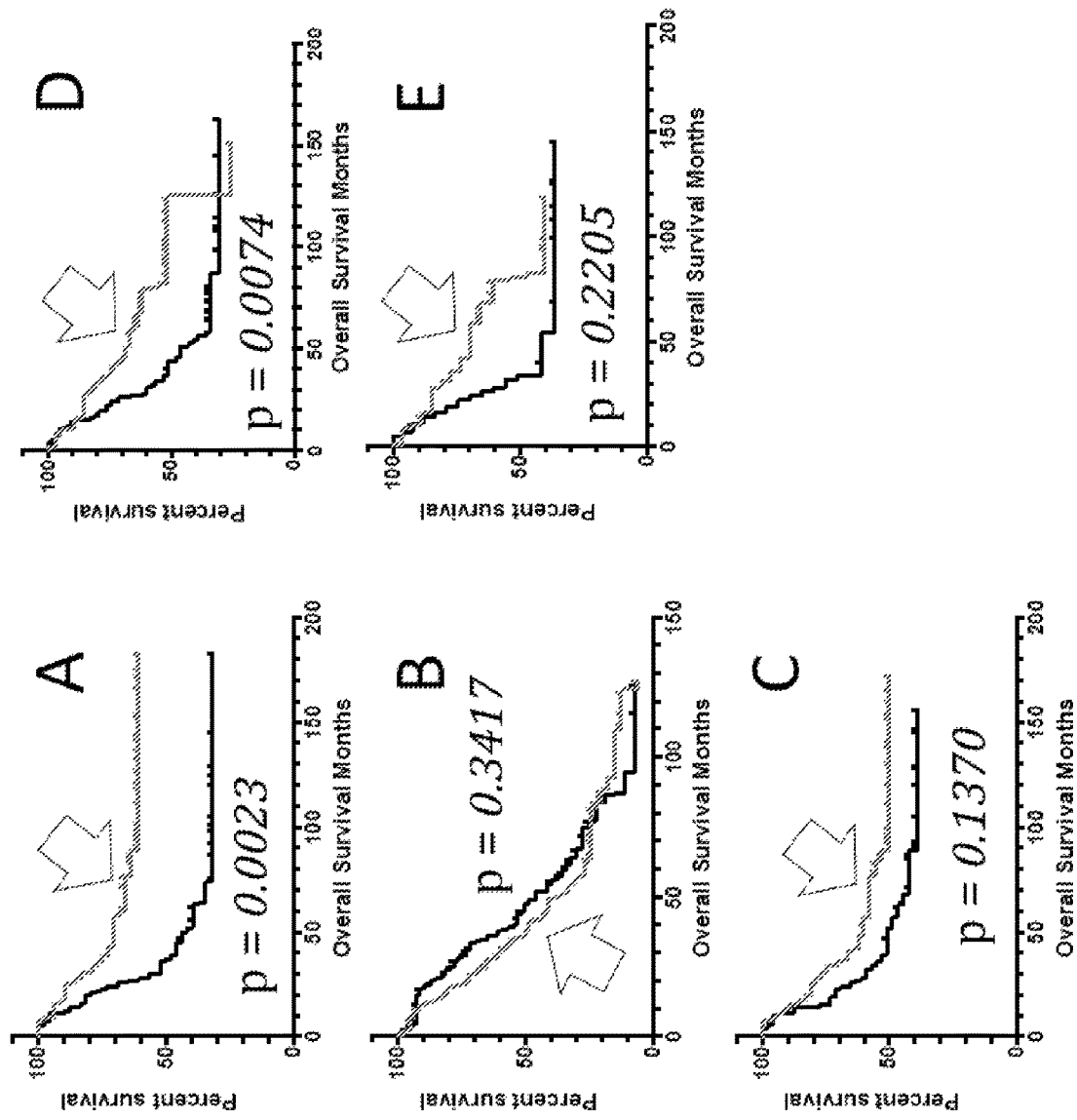
FIG. 6A, FIG. 6B, FIG. 6C, FIG. 6D, and FIG. 6E

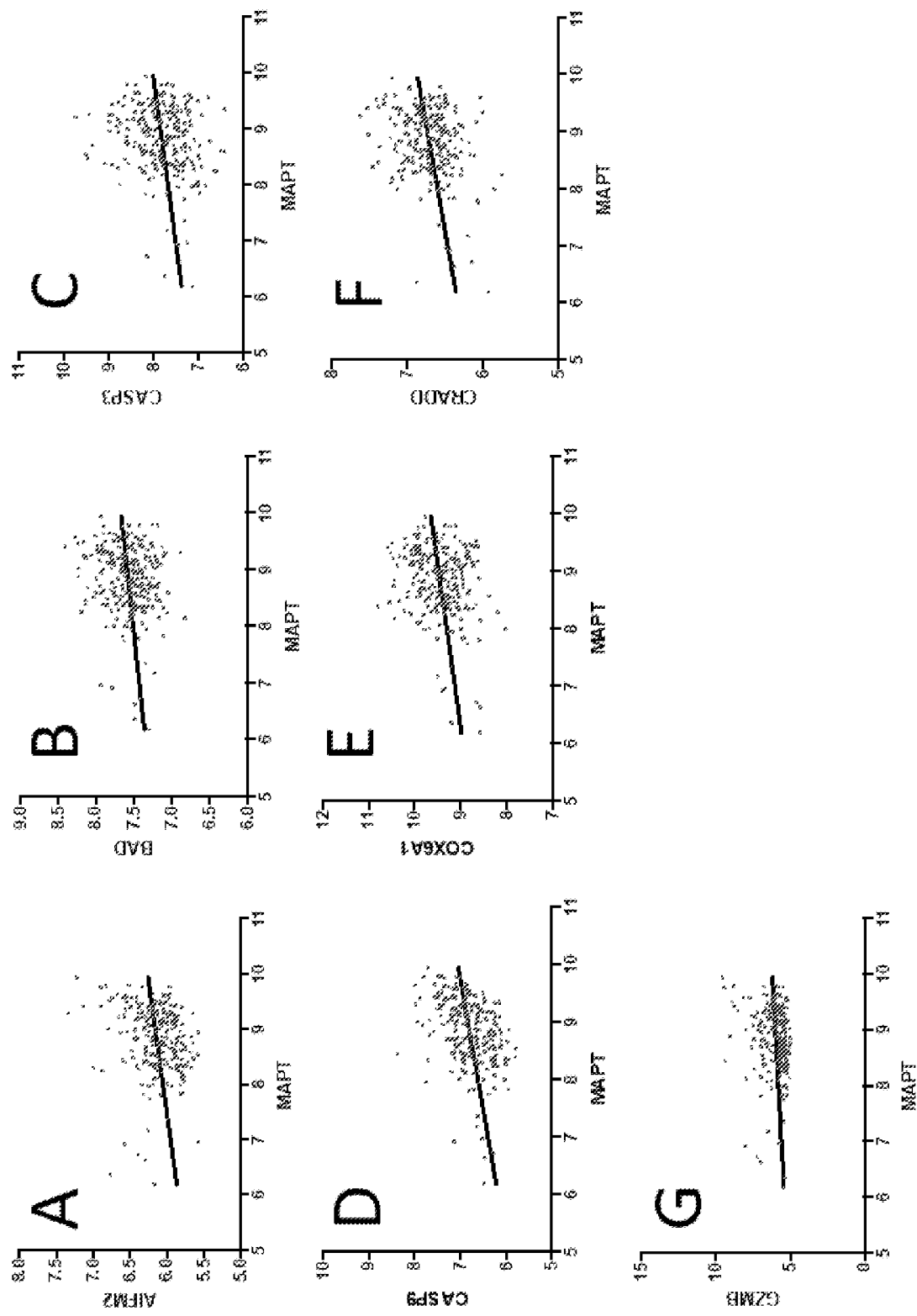
FIG. 7A, FIG. 7B, FIG. 7C, FIG. 7D, FIG. 7E, FIG. 7F, and FIG. 7G

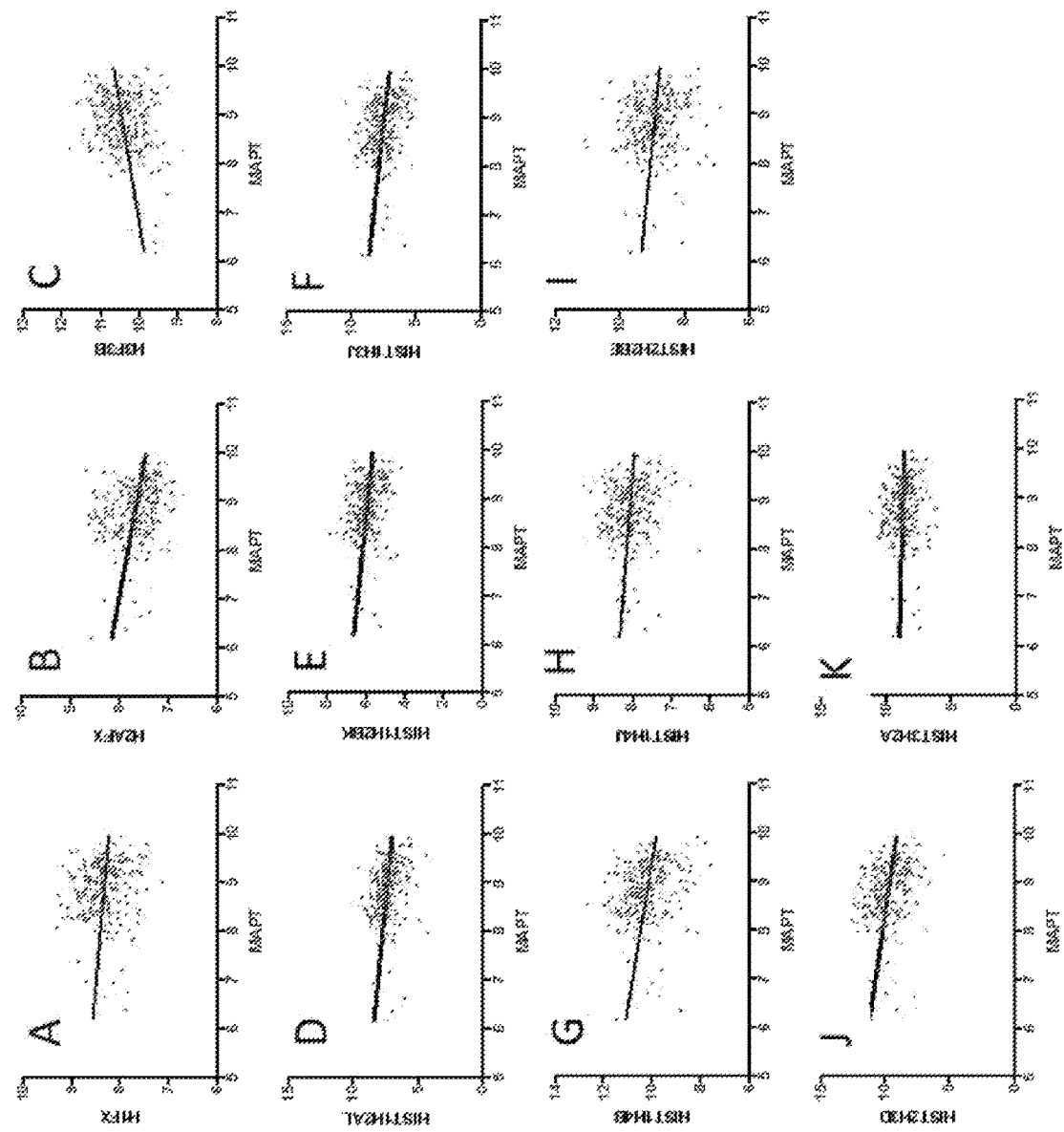
FIG. 9A, FIG. 9B, FIG. 9C, FIG. 9D, FIG. 9E, FIG. 9F, FIG. 9G, FIG. 9H, FIG. 9I, FIG. 9J, and FIG. 9K

BIOMARKERS OF LOW GRADE GLIOMA AND PEDIATRIC NEUROBLASTOMA

CROSS-REFERENCE TO RELATED APPLICATIONS

This application is a Divisional of U.S. patent application Ser. No. 16/580,644, filed Sep. 24, 2019, which depends from and claims priority to U.S. Provisional Application No. 62/735,230, filed Sep. 24, 2018, which are incorporated by reference in their entirety for all purposes.

FIELD

The present disclosure relates to biomarkers and methods for determining or predicting survival of patients with low grade glioma (LGG) or pediatric neuroblastoma. Further disclosed are methods of diagnosing and treating patients with low grade glioma (LGG) or pediatric neuroblastoma.

BACKGROUND

The MAPT gene (Microtubule Associated Protein—Tau) encodes the tau protein, which is involved in microtubule stabilization and tubulin polymerization into microtubules. It has long been established that aggregations of hyperphosphorylated neurofibrillary and gliofibrillary tangles of tau protein are involved in several neurodegenerative disorders, known as tauopathies. However, the role of tau in brain cancers (for example, low-grade glioma) and cancers of neuronal origin (for example, pediatric neuroblastoma) has not been explored.

Gliomas are histologically graded from I to IV. Grade I gliomas are usually benign. Grade II (Low Grade Glioma (LGG)) has an average survival period of approximately 7 years. Grade II gliomas can progress into grade III (high grade gliomas), and eventually grade IV (secondary glioblastoma). Recent research indicates that historically used clinical variables in LGG are inferior prognostic indicators relative to current genetic information, for example IDH1 mutational status. As LGG is an early stage in the progression of gliomas from low grade to high grade, there is a need to understand the disease process from this early onset. Pinpointing key molecular features that are associated with improved outcomes will help elucidate the disease progression and serve as prognostic markers in the clinic.

Neuroblastoma is an aggressive pediatric cancer of neuronal origin that causes approximately 13% of all pediatric cancer deaths and is the primary cause of cancer-related death for children between the ages of one and five years. It is the third most common pediatric cancer, after leukemia and brain cancers. Furthermore, neuroblastoma tumors are able to mature spontaneously, and there are certain phenotypes, dubbed "ultra-high risk" that tend to have increased resistance to therapy. The International Neuroblastoma Risk Group classification system was developed to aid in the clinical management of pediatric neuroblastoma. Based on molecular and clinical features, patients are grouped into either low, intermediate, or high risk groups, with high risk groups having poor survival outcomes. Thus, there is a need to identify biological characteristics that may help better inform clinicians regarding the risk-status of the neuroblastoma patients.

The methods disclosed herein address these and other needs.

SUMMARY

Disclosed herein are methods for determining or predicting survival of patients with low grade glioma (LGG) based on expression levels of MAPT (Tau), CASP9, or UQCRC2. Further disclosed are methods of diagnosing and treating patients with low grade glioma (LGG) based on expression levels of MAPT (Tau), CASP9, or UQCRC2.

Also disclosed herein are methods for determining or predicting survival of patients with pediatric neuroblastoma based on expression levels of MAPT (Tau), CASP3, or CASP9. Further disclosed are methods of diagnosing and treating patients with pediatric neuroblastoma based on expression levels of MAPT (Tau), CASP3, or CASP9.

While the association of MAPT (Tau) with various tauopathies and other neurological disorders has long been established, the role of MAPT expression in brain cancers and cancers of neuronal origin are unknown. Surprisingly, the inventors determined that high expression of the MAPT gene is strongly associated with increased overall and disease free survival in low grade glioma (LGG) and pediatric neuroblastoma, but not in breast cancer, melanoma, or ovarian cancer. Thus, these methods improve upon existing methods for the diagnosis and treatment of LGG patients and pediatric neuroblastoma patients by determining the expression levels of a biomarker more conventionally associated with neurological disorders. These unexpected findings (for MAPT (Tau) and several additional biomarkers) are used for determining and predicting survival of subjects with LGG or pediatric neuroblastoma, allowing treatment with the appropriate chemotherapeutic regimens.

In some aspects, disclosed herein is a method for determining or predicting the overall survival of a subject having low grade glioma (LGG), comprising:
obtaining a biological sample derived from the subject having LGG;
quantifying an expression level of one or more biomarkers that are associated with overall survival in low grade glioma (LGG) in the biological sample derived from the subject relative to a reference control, wherein the biomarker comprises one or more of MAPT, CASP9, and UQCRC2; and
determining or predicting one of:
  a. the subject as having a shorter overall survival if the expression level of one or more of the biomarkers MAPT, CASP9, and UQCRC2 is lower in the biological sample derived from the subject compared to the reference control, or
  b. the subject as having a longer overall survival if the expression level of one or more of the biomarkers MAPT, CASP9, and UQCRC2 is higher in the biological sample derived from the subject compared to the reference control.

In other aspects, disclosed herein is a method of treating a subject having low grade glioma (LGG), comprising:
obtaining a biological sample derived from the subject having LGG;
quantifying an expression level of one or more biomarkers that are associated with overall survival in low grade glioma (LGG) in the biological sample derived from the subject relative to a reference control, wherein the biomarker comprises one or more of MAPT, CASP9, and UQCRC2;
determining or predicting the subject as having a shorter overall survival if the expression level of one or more of the biomarkers MAPT, CASP9, and UQCRC2 is lower in the biological sample derived from the subject compared to the reference control; and
administering to the subject a therapeutically effective amount of an activator of MAPT, an activator of CASP9, an activator of UQCRC2, or a combination thereof.

In some aspects, disclosed herein is a method for determining or predicting the overall survival of a subject having pediatric neuroblastoma, comprising:
quantifying an expression level of one or more biomarkers that are associated with overall survival in pediatric neuroblastoma in the biological sample derived from the subject relative to a reference control, wherein the biomarker comprises one or more of MAPT, CASP3, and CASP9; and
determining or predicting one of:
  a. the subject as having a shorter overall survival if the expression level of one or more of the biomarkers MAPT, CASP3, and CASP9 is lower in the biological sample derived from the subject compared to the reference control, or
  b. the subject as having a longer overall survival if the expression level of one or more of the biomarkers MAPT, CASP3, and CASP9 is higher in the biological sample derived from the subject compared to the reference control.

In other aspects, disclosed herein is a method of treating a subject having pediatric neuroblastoma, comprising:
obtaining a biological sample derived from the subject having pediatric neuroblastoma;
quantifying an expression level of one or more biomarkers that are associated with overall survival in pediatric neuroblastoma in the biological sample derived from the subject relative to a reference control, wherein the biomarker comprises one or more of MAPT, CASP3, and CASP9;
determining or predicting the subject as having a shorter overall survival if the expression level of one or more of the biomarkers MAPT, CASP3, and CASP9 is lower in the biological sample derived from the subject compared to the reference control; and
administering to the subject a therapeutically effective amount of an activator of MAPT, an activator of CASP3, an activator of CASP9, or a combination thereof.

BRIEF DESCRIPTION OF THE DRAWINGS

The accompanying figures, which are incorporated in and constitute a part of this specification, illustrate several aspects described below.

(FIG. 1A) Kaplan-Meier (KM) overall survival (OS) curve for low-grade glioma (LGG) barcodes that are in the top quintile of MAPT expressers (n=96, arrow), compared to the OS for the bottom quintile of MAPT expressers (n=104). Mean OS for the top quintile of MAPT expressers, 109.04 months; mean OS for bottom quintile of MAPT expressers, 59.36 months. Log rank comparison p-value, p=9.152E-10. (FIG. 1B) KM OS analysis for skin cutaneous melanoma (SKCM) barcodes that are in the top quintile of MAPT expressers (n=90, arrow), compared to the OS for the bottom quintile of MAPT expressers (n=91). Mean OS for the top quintile of MAPT expressers, 108.85 months; mean OS for bottom quintile of MAPT expressers, 131.09 months. Log rank comparison p-value, p=0.433. (FIG. 1C) KM OS analysis for breast cancer (BRCA) barcodes that are in the top quintile of MAPT expressers (n=218, arrow), compared to the OS for the bottom quintile of MAPT expressers (n=218). Mean OS for the top quintile of MAPT expressers, 154.70 months; mean OS for bottom quintile of MAPT expressers, 164.95 months. Log rank comparison p-value, p=0.302. (FIG. 1D) KM disease-free survival (DFS) analysis for LGG barcodes that are in the top quintile of MAPT expressers (n=93, arrow), compared to the DFS for the bottom quintile of MAPT expressers (n=86). Mean DFS for the top quintile of MAPT expressers, 74.72 months; mean DFS for bottom quintile of MAPT expressers, 34.80 months. Log rank comparison p-value, p=2.215E-10. (FIG. 1E) KM DFS analysis for SKCM barcodes that are in the top quintile of MAPT expressers (n=76, arrow), compared to the DFS for the bottom quintile of MAPT expressers (n=80). Mean DFS for the top quintile of MAPT expressers, 71.36 months; mean DFS for bottom quintile of MAPT expressers, 73.59 months. Log rank comparison p-value, p=0.975. (FIG. 1F) KM DFS analysis for BRCA barcodes that are in the top quintile of MAPT expressers (n=200, arrow), compared to the DFS for the bottom quintile of MAPT expressers (n=198). Mean DFS for the top quintile of MAPT expressers, 169.72 months; mean DFS for bottom quintile of MAPT expressers, 192.60 months. Log rank comparison p-value, p=0.316.

(FIG. 2A) KM OS analysis for LGG barcodes that are in the top quintile of SNCA expressers (n=105, arrow), compared to the OS for the bottom quintile of SNCA expressers (n=100). Mean OS for the top quintile of MAPT expressers, 89.44 months; mean OS for bottom quintile of MAPT expressers, 82.74 months. Log rank comparison p-value, p=0.279. (FIG. 2B) KM OS analysis for LGG barcodes that are in the top quintile of APP expressers (n=102, arrow), compared to the OS for the bottom quintile of APP expressers (n=102). Mean OS for the top quintile of MAPT expressers, 134.17 months; mean OS for bottom quintile of MAPT expressers, 138.93 months. Log rank comparison p-value, p=0.565.

FIG. 3A-3E. Correlation of MAPT and apoptosis-effector gene expression levels. Results here indicated correlation of high MAPT expression levels with high apoptosis-effector gene expression levels. (FIG. 3A) MAPT vs. CASP9; X-axis range: 0-30000; Y-axis range: 0-3500; (FIG. 3B) MAPT vs. COX7A2L; X-axis range: 0-30,000; Y-axis range: 0-3500; (FIG. 3C) MAPT vs. CRADD; x-axis range: 0-30000; y-axis range: 0-600; (FIG. 3D) MAPT vs. CYC1; x-axis range: 0-30000; (FIG. 3E) MAPT vs. UQCRC2; X-axis range: 0-30000; Y-axis range: 0-10000. The p-values for the Pearson Correlation Coefficients are p<0.00001, p=0.00723, p=0.02863, p=0.00169 and p<0.00001 respectively for each relationship.

(FIG. 4A) KM OS curve for LGG barcodes that are in the top quintile of CASP9 expressers (n=100, arrow), compared to the OS for the bottom quintile of CASP9 expressers (n=105). Mean OS for the top quintile of CASP9 expressers, 105.309 months; mean OS for bottom quintile of CASP9 expressers, 73.471 months. Log rank comparison p-value, p=0.000014. (FIG. 4B) KM overall survival (OS) curve for LGG barcodes that are in the top quintile of UQCRC2 expressers (n=103, arrow), compared to the OS for the bottom quintile of UQCRC2 expressers (n=103). Mean OS for the top quintile of UQCRC2 expressers, 115.495 months; mean OS for bottom quintile of UQCRC2 expressers, 48.623 months. Log rank comparison p-value, p=1.971E-7.

FIG. 5A-5C. Inverse correlation of MAPT and proliferation-effector gene expression levels. (FIG. 5A) MAPT vs. H2AFX; X-axis: 0-30000; Y-axis: 0-16000; (FIG. 5B) MAPT vs. HIST1H2BK; X-axis: 0-30000; Y-axis: 0-2000; (FIG. 5C) MAPT vs. HIST2H2BE; X-axis: 0-30000; Y-axis: 0-6000. The p-values for the Pearson Correlation Coefficient are p<0.00001, p<0.00001, and p=0.000727, respectively for each relationship.

FIG. 6A-6E. Kaplan-Meier curves representing distinct MAPT gene expression levels. Results presented here were consistent with increased tumor cell replication in cases of lower MAPT expression and reduced survival rates. (FIG. 6A) Kaplan-Meier (KM) overall survival (OS) curve representing pediatric neuroblastoma barcode microarray values in the top quintile of MAPT expressers (n=48, gray, arrow), compared to the OS for the bottom quintile of MAPT expressers (n=49, black). Mean OS for the top quintile of MAPT expressers, undefined months; mean OS for bottom quintile of MAPT expressers, 37 months. Log rank comparison p-value=0.0023. (FIG. 6B) KM OS curve for ovarian serous cystadenocarcinoma (OV) barcode microarray values in the top quintile of MAPT expressers (n=103, gray, arrow), compared to the OS for the bottom quintile of MAPT expressers (n=102, black). Mean OS for the top quintile of MAPT expressers, 38.40 months; mean OS for bottom quintile of MAPT expressers, 47.57 months. Log rank comparison p-value=0.3471 (not significant). (FIG. 6C) KM OS curve for pediatric neuroblastoma barcode microarray values in the top quintile of SNCA expressers (n=48, gray, arrow), compared to the OS for the bottom quintile of SNCA expressers (n=49, black). Mean OS for the top quintile of SNCA expressers, undefined months; mean OS for bottom quintile of SNCA expressers, 52 months. Log rank comparison p-value=0.1370 (not significant). (FIG. 6D) KM OS curve for pediatric neuroblastoma barcode RNAseq values in the top half of MAPT expressers (n=68, gray, arrow), compared to the OS for the bottom half of MAPT expressers (n=66, black). Mean OS for the top half of MAPT expressers, 125 months; mean OS for bottom half of MAPT expressers, 44 months. Log rank comparison p-value=0.0074. (FIG. 6E) KM OS curve for pediatric neuroblastoma barcode RNAseq values in the top quintile of MAPT expressers (n=27, gray, arrow), compared to the OS for the bottom quintile of MAPT expressers (n=28, black). Mean OS for the top quintile of MAPT expressers, 80 months; mean OS for bottom quintile of MAPT expressers, 34 months. Log rank comparison p-value=0.2205.

FIG. 7A-7G. Correlation of MAPT and apoptosis-effector gene expression levels. MAPT microarray expression vs. apoptosis-effector gene microarray expression. The p-values for the Pearson Correlation Coefficients are presented after each relationship, respectively. (FIG. 7A) MAPT vs. AIFM2; p=0.0008; (FIG. 7B) MAPT vs. BAD; p=0.0051; (FIG. 7C) MAPT vs. CASP3; p=0.0050; (FIG. 7D) MAPT vs. CASP9; p<0.0001; (FIG. 7E) MAPT vs. COX6A1; p=0.0005; (FIG. 7F) MAPT vs. CRADD; p<0.0001; (FIG. 7G) MAPT vs. GZMB; p=0.0205.

(FIG. 8A) KM OS curve for pediatric neuroblastoma barcode microarray values in the top quintile of CASP3 expressers (n=49, gray, arrow), compared to the OS for the bottom quintile of CASP3 expressers (n=49, black). Mean OS for the top quintile of CASP3 expressers, undefined months; mean OS for bottom quintile of CASP3 expressers, 37 months. Log rank comparison p-value, p=0.0052. (FIG. 8B) KM OS curve for pediatric neuroblastoma barcode microarray values in the top quintile of CASP9 expressers (n=49, gray, arrow), compared to the OS for the bottom quintile of CASP9 expressers (n=49, black). Mean OS for the top quintile of CASP9 expressers, undefined months; mean OS for bottom quintile of CASP9 expressers, 38.5 months. Log rank comparison p-value, p=0.0353.

FIG. 9A-9K. Correlation of MAPT and proliferation-effector gene expression levels. MAPT microarray expression vs. proliferation-effector gene microarray expression. The p-values for the Pearson Correlation Coefficient are presented after each relationship respectively. (FIG. 9A) MAPT vs. H1FX; p=0.0355; (FIG. 9B) MAPT vs. H2AFX; p<0.0001; (FIG. 9C) MAPT vs. H3F3B; p<0.0001; (FIG. 9D) MAPT vs. HIST1H2AL; p<0.0001; (FIG. 9E) MAPT vs. HIST1H2BK; p<0.0001; (FIG. 9F) MAPT vs. HIST1H3J; p<0.0001; (FIG. 9G) MAPT vs. HIST1H4B; p=0.0001; (FIG. 9H) MAPT vs. HIST1H4J; p=0.0346; (FIG. 9I) MAPT vs. HIST2H2BE; p=0.0285; (FIG. 9J) MAPT vs. HIST2H3D; p<0.0001; (FIG. 9K) MAPT vs. HIST3H2A; p=0.3062.

(FIG. 10A) KM OS curve for pediatric neuroblastoma barcode microarray values in the top quintile of H1FX expressers (n=49, gray), compared to the OS for the bottom quintile of H1FX expressers (n=49, black). Mean OS for the top quintile of H1FX expressers, 27 months; mean OS for bottom quintile of H1FX expressers, 83 months. Log rank comparison p-value, p=0.0443. (FIG. 10B) KM OS curve for pediatric neuroblastoma barcode microarray values in the top quintile of HIST2H3D expressers (n=49, gray), compared to the OS for the bottom quintile of HIST2H3D expressers (n=49, black). Mean OS for the top quintile of HIST2H3D expressers, 48 months; mean OS for bottom quintile of HIST2H3D expressers, undefined months. Log rank comparison p-value=0.0377.

(FIG. 12A) KM OS curve for pediatric neuroblastoma barcode microarray values in the top quintile of APP expressers (n=48, gray), compared to the OS for the bottom quintile of APP expressers (n=49, black). Mean OS for the top quintile of APP expressers, 125 months; mean OS for bottom quintile of APP expressers, 31 months. Log rank comparison p-value=0.0112. (FIG. 12B) KM OS curve for pediatric neuroblastoma barcode microarray values in the top quintile of TARDBP expressers (n=49, gray), compared to the OS for the bottom quintile of TARDBP expressers (n=49, black). Mean OS for the top quintile of TARDBP expressers, undefined months; mean OS for bottom quintile of APP expressers, 35 months. Log rank comparison p-value=0.0237.

DETAILED DESCRIPTION

Figure 1A:
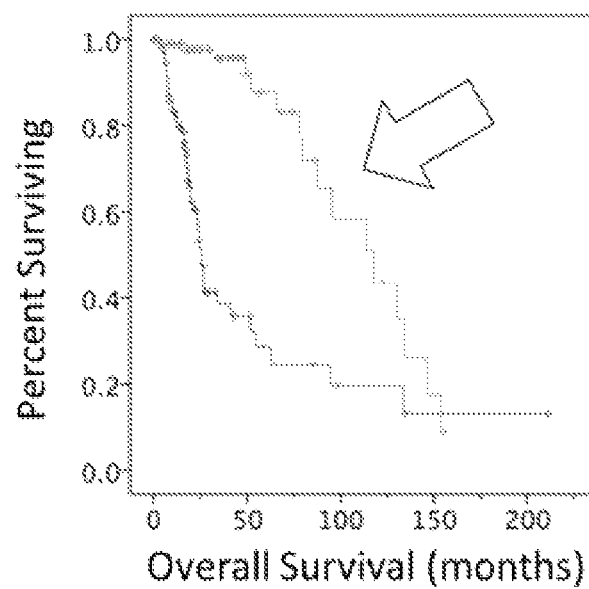
FIGS. 1A-1F. Kaplan-Meier curves representing distinct MAPT expression levels. Results here indicated that there were overall and disease-free survival distinctions for LGG based on the MAPT levels in the patient tumors. However, no such distinctions were detectable in BRCA and SKCM tumor samples. The following text provides mean survival times and p-values for the Kaplan-Meier analyses.
Figure 1B:
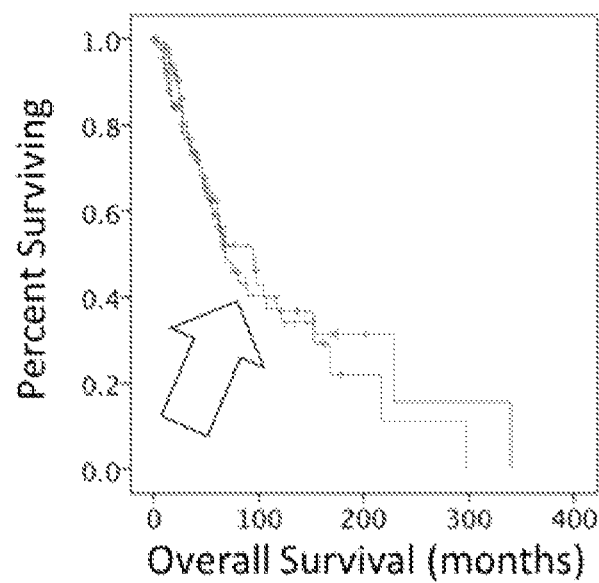
Figure 1C:
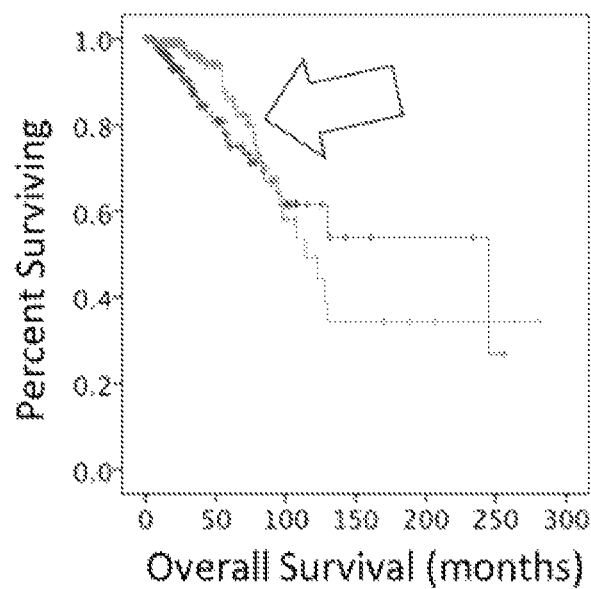
Figure 1D:
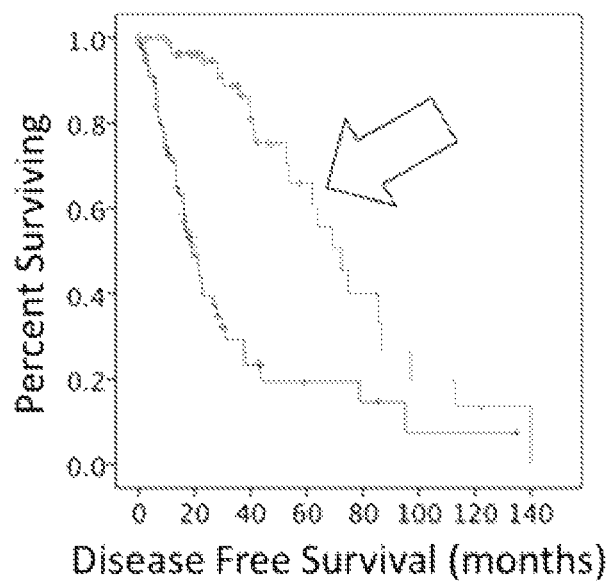
Figure 1E:
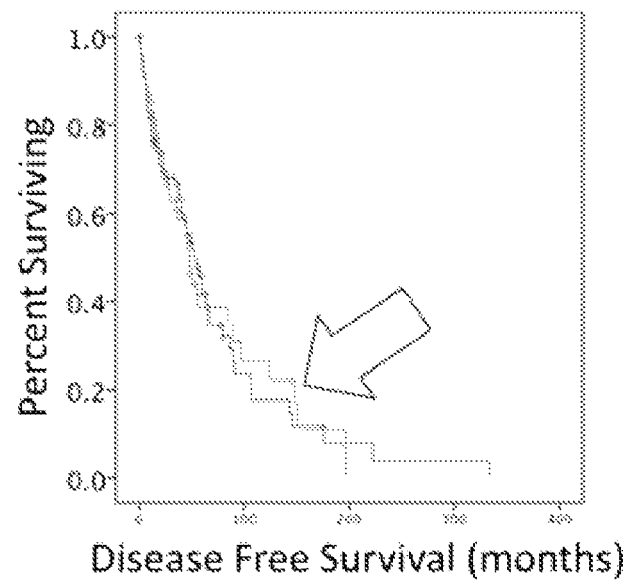
Figure 1F:
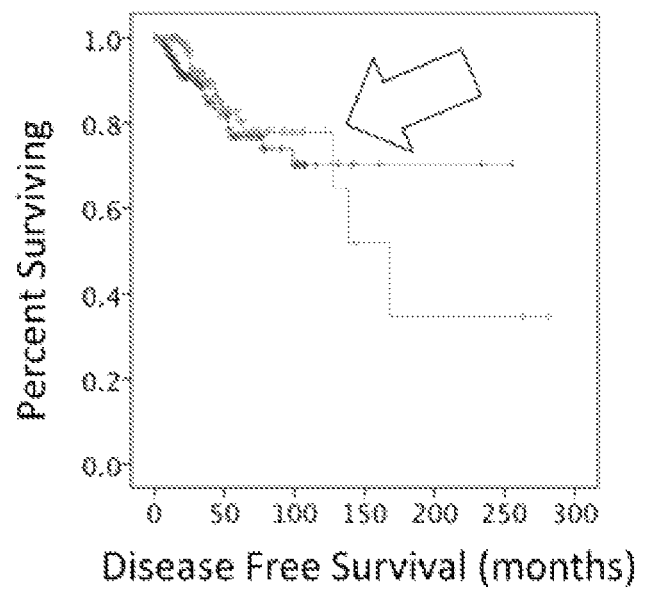

Disclosed herein are methods for determining or predicting survival of patients with low grade glioma (LGG) based on expression levels of MAPT (Tau), CASP9, or UQCRC2. Further disclosed are methods of diagnosing and treating patients with low grade glioma (LGG) based on expression levels of MAPT (Tau), CASP9, or UQCRC2.

Also disclosed herein are methods for determining or predicting survival of patients with pediatric neuroblastoma based on expression levels of MAPT (Tau), CASP3, or CASP9. Further disclosed are methods of diagnosing and treating patients with pediatric neuroblastoma based on expression levels of MAPT (Tau), CASP3, or CASP9.

While the association of MAPT (Tau) with various tauopathies and other neurological disorders has long been established, the role of MAPT expression in brain cancers and cancers of the nervous system are unknown. Surprisingly, the inventors determined that high expression of the MAPT gene is strongly associated with increased overall and disease free survival in low grade glioma (LGG) and pediatric neuroblastoma, but not in breast cancer, melanoma, or ovarian cancer. Thus, these methods improve upon existing methods for the diagnosis and treatment of LGG patients and pediatric neuroblastoma patients by determining the expression levels of a biomarker more conventionally associated with neurological disorders. Thus, these unexpected findings (for MAPT (Tau) and several additional biomarkers) are used for determining and predicting survival of subjects with LGG or pediatric neuroblastoma, allowing treatment with the appropriate chemotherapeutic regimens.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition (e.g. LGG or pediatric neuroblastoma). The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder (e.g. LGG or pediatric neuroblastoma), or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount." However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition (e.g. LGG or pediatric neuroblastoma). Therapeutically effective and prophylactically effective amounts of a given therapeutic agent will typically vary with respect to factors such as the type and severity of the disorder or disease being treated and the age, gender, and weight of the subject.

The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

The term "subject" or "host" refers to any individual who is the target of administration or treatment. The subject can be a vertebrate, for example, a mammal. Thus, the subject can be a human or veterinary patient. The term "patient" refers to a subject under the treatment of a clinician, e.g., physician. The subject can be either male or female.

The terms "peptide," "protein," and "polypeptide" are used interchangeably to refer to a natural or synthetic molecule comprising two or more amino acids linked by the carboxyl group of one amino acid to the alpha amino group of another.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T/U, or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, at least about 75%, or at least about 90% complementary. See Kanehisa (1984) Nucl. Acids Res. 12:203.

"Hybridization" refers to the process in which two single-stranded oligonucleotides bind non-covalently to form a stable double-stranded oligonucleotide. The term "hybridization" may also refer to triple-stranded hybridization. The resulting (usually) double-stranded oligonucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. In certain exemplary embodiments, hybridization takes place at room temperature. The term "stringent hybridization conditions" as used herein is the binding which occurs within a range from about Tm 5° C. (5° C. below the melting temperature Tm of the probe) to about 20° C. to 25° C. below Tm. The term "highly stringent hybridization conditions" as used herein refers to conditions of: at least about 6x SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

The term "activator of MAPT (Tau)" refers to a substance that increases expression levels or activity of MAPT (Tau). The term "activator of CASP9" refers to a substance that increases expression levels or activity of CASP9. The term "activator of UQCRC2" refers to a substance that increases expression levels or activity of UQCRC2. The term "activator of CASP3" refers to a substance that increases expression levels or activity of CASP3. Likewise, an activator of another gene/protein refers to a substance that increases expression levels or activity of the corresponding gene/protein.

Methods of Diagnosis and Treatment

In some aspects, disclosed herein is a method for determining or predicting the overall survival of a subject having low grade glioma (LGG), comprising:

obtaining a biological sample derived from the subject having LGG;

quantifying an expression level of one or more biomarkers that are associated with overall survival in low grade glioma (LGG) in the biological sample derived from the subject relative to a reference control, wherein the biomarker comprises one or more of MAPT, CASP9, and UQCRC2; and determining or predicting one of:
  a. the subject as having a shorter overall survival if the expression level of one or more of the biomarkers MAPT, CASP9, and UQCRC2 is lower in the biological sample derived from the subject compared to the reference control, or
  b. the subject as having a longer overall survival if the expression level of one or more of the biomarkers MAPT, CASP9, and UQCRC2 is higher in the biological sample derived from the subject compared to the reference control.

In some embodiments, the biomarker comprises MAPT. In some embodiments, the biomarker comprises CASP9. In some embodiments, the biomarker comprises UQCRC2.

In some embodiments, the biological sample comprises one or a combination of brain tumor tissue, brain tumor cells, or biopsy tissue. In some embodiments, the biological sample comprises a blood sample.

In some embodiments, the quantifying is carried out to detect gene expression levels. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the quantifying is carried out to detect protein expression levels. In some embodiments, the quantifying is carried out by one or a combination of Western blot, ELISA, flow cytometry, immunohistochemistry, and other methods of detection using antibodies (for example, antibodies to recognize the MAPT (Tau), CASP9, or UQCRC2 biomarker proteins).

In some embodiments, the quantifying is carried out to detect gene methylation and gene copy number. For example, with low MAPT, there may be loss of DNA that is the cause of low MAPT, or methylation of the MAPT gene may reduce MAPT expression.

In some embodiments, the reference control is the expression level of the appropriate biomarker for the lowest quintile (20%) of the biomarker levels of a reference population of low grade glioma patient samples. In some embodiments, the reference control is the expression level of the appropriate biomarker for the highest quintile (20%) of the biomarker levels of a reference population of low grade glioma patient samples.

In some embodiments, the reference control is the expression level of the appropriate biomarker for the lowest 10%, 20%, 30%, 40%, or 50% of the biomarker levels of a reference population of low grade glioma patient samples. In some embodiments, the reference control is the expression level of the appropriate biomarker for the highest 10%, 20%, 30%, 40%, or 50% of the biomarker levels of a reference population of low grade glioma patient samples.

In some embodiments, the method further comprises administering an appropriate LGG therapy to the subject based on the prediction of the subject as having a shorter overall survival. In some embodiments, the method further comprises administering an appropriate LGG therapy to the subject based on the prediction of the subject as having an overall survival of 59 months or less. In some embodiments, the method further comprises administering an appropriate LGG therapy to the subject based on the prediction of the subject as having an overall survival of 73 months or less.

In some embodiments, the method further comprises administering an appropriate LGG therapy to the subject based on the prediction of the subject as having an overall survival of about 35 months or less, about 40 months or less, about 45 months or less, about 50 months or less, about 55 months or less, about 60 months or less, about 65 months or less, about 70 months or less, about 75 months or less, about 80 months or less, about 85 months or less, about 90 months or less, about 95 months or less, or about 100 months or less.

In some embodiments, the method further comprises: administering an activator of MAPT, an activator of CASP9, an activator of UQCRC2, or a combination thereof. In some embodiments, the method further comprises: administering an activator of MAPT. In some embodiments, the activator of MAPT is cordycepin. In some embodiments, the activator of MAPT is a cordycepin derivative (see for example, U.S. Pat. Nos. 6,949,521 or 5,550,111). In some embodiments, the activator of MAPT is fenretinide.

Cordycepin is an adenosine analogue (3'-deoxyadenosine). In some embodiments, additional adenosine analogues or other nucleoside analogues can be used.

In some embodiments, the appropriate LGG therapy is administered in a therapeutically effective amount. In some embodiments, the activator of MAPT, the activator of CASP9, the activator of UQCRC2, or the combination thereof, is administered in a therapeutically effective amount.

In some embodiments, the LGG therapy can raise ceramide levels. Ceramides are known to raise tau levels and thus activators of ceramide levels can be used as activators of tau (for example, fenretinide or see U.S. Pat. No. 8,143,313). In some embodiments, the LGG therapy can include compounds that are microtubule stabilizing agents, as tau is known to stabilize microtubules (for example, paclitaxel or docetaxel).

In some embodiments, the subject is a human.

In some aspects, disclosed herein is a method for determining or predicting the overall survival of a subject having low grade glioma (LGG), comprising:

quantifying an expression level of one or more biomarkers that are associated with overall survival in low grade glioma (LGG) in the biological sample derived from the subject relative to a reference control, wherein the biomarker comprises one or more of MAPT, CASP9, and UQCRC2; and determining or predicting one of:
  a. the subject as having a shorter overall survival if the expression level of one or more of the biomarkers MAPT, CASP9, and UQCRC2 is lower in the biological sample derived from the subject compared to the reference control, or
  b. the subject as having a longer overall survival if the expression level of one or more of the biomarkers MAPT, CASP9, and UQCRC2 is higher in the biological sample derived from the subject compared to the reference control.

In some aspects, disclosed herein is a method for determining or predicting the disease-free survival of a subject having low grade glioma (LGG), comprising:

obtaining a biological sample derived from the subject having LGG;

quantifying an expression level of one or more biomarkers that are associated with disease-free survival in low grade glioma (LGG) in the biological sample derived from the subject relative to a reference control, wherein the biomarker comprises one or more of MAPT, CASP9, and UQCRC2; and determining or predicting one of:
  a. the subject as having a shorter disease-free survival if the expression level of one or more of the biomarkers MAPT, CASP9, and UQCRC2 is lower in the biological sample derived from the subject compared to the reference control, or
  b. the subject as having a longer disease-free survival if the expression level of one or more of the biomarkers MAPT, CASP9, and UQCRC2 is higher in the biological sample derived from the subject compared to the reference control.

In other aspects, disclosed herein is a method of treating a subject having low grade glioma (LGG), comprising:

obtaining a biological sample derived from the subject having LGG;

quantifying an expression level of one or more biomarkers that are associated with overall survival in low grade glioma (LGG) in the biological sample derived from the subject relative to a reference control, wherein the biomarker comprises one or more of MAPT, CASP9, and UQCRC2;

determining or predicting the subject as having a shorter overall survival if the expression level of one or more of the biomarkers MAPT, CASP9, and UQCRC2 is lower in the biological sample derived from the subject compared to the reference control; and administering to the subject a therapeutically effective amount of an activator of MAPT, an activator of CASP9, an activator of UQCRC2, or a combination thereof.

In some embodiments, the biomarker comprises MAPT. In some embodiments, the biomarker comprises CASP9. In some embodiments, the biomarker comprises UQCRC2.

In some embodiments, the biological sample comprises one or a combination of brain tumor tissue, brain tumor cells, or biopsy tissue. In some embodiments, the biological sample comprises a blood sample.

In some embodiments, the quantifying is carried out to detect gene expression levels. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the quantifying is carried out to detect protein expression levels. In some embodiments, the quantifying is carried out by one or a combination of Western blot, ELISA, flow cytometry, and other methods of detection using antibodies (for example, antibodies to recognize the MAPT (Tau), CASP9, or UQCRC2 biomarker proteins).

In some embodiments, the reference control is the expression level of the appropriate biomarker for the lowest quintile (20%) of the biomarker levels of a reference population of low grade glioma patient samples. In some embodiments, the reference control is the expression level of the appropriate biomarker for the highest quintile (20%) of the biomarker levels of a reference population of low grade glioma patient samples.

In some embodiments, the method further comprises administering an appropriate LGG therapy to the subject based on the prediction of the subject as having a shorter overall survival. In some embodiments, the method further comprises administering an appropriate LGG therapy to the subject based on the prediction of the subject as having an overall survival of 59 months or less. In some embodiments, the method further comprises administering a differing amount of appropriate LGG therapy to a patient based on the level of biomarker expression (MAPT (Tau), CASP9, or UQCRC2 biomarkers). For example, patients with relatively lower levels of MAPT (Tau) expression would be administered higher amounts of LGG therapy (for example, cordycepin), while patients with relatively higher levels of expression of MAPT (Tau) expression would be administered lower amounts of LGG therapy (for example, cordycepin).

In some embodiments, the method further comprises: administering an activator of MAPT, an activator of CASP9, an activator of UQCRC2, or a combination thereof. In some embodiments, the method further comprises: administering an activator of MAPT. In some embodiments, the activator of MAPT is cordycepin. In some embodiments, the activator of MAPT is a cordycepin derivative (see for example, U.S. Pat. Nos. 6,949,521 or 5,550,111). In some embodiments, the activator of MAPT is fenretinide.

In some embodiments, the subject is a human.

In other aspects, disclosed herein is a method of treating a subject having low grade glioma (LGG), comprising:
quantifying an expression level of one or more biomarkers that are associated with overall survival in low grade glioma (LGG) in the biological sample derived from the subject relative to a reference control, wherein the biomarker comprises one or more of MAPT, CASP9, and UQCRC2;

determining or predicting the subject as having a shorter overall survival if the expression level of one or more of the biomarkers MAPT, CASP9, and UQCRC2 is lower in the biological sample derived from the subject compared to the reference control; and administering to the subject a therapeutically effective amount of an activator of MAPT, an activator of CASP9, an activator of UQCRC2, or a combination thereof.

In some embodiments, the biomarker comprises MAPT. In some embodiments, the biomarker comprises CASP9. In some embodiments, the biomarker comprises UQCRC2.

In some embodiments, the level of the one or more of the biomarkers MAPT, CASP9, and UQCRC2 determines the subject as having a 10% or more (for example 10% or more, 20% or more, 30% or more, 40% or more, 50% or more, 60% or more, 70% or more, 80% or more, 90% or more, 100% or more) increase in survival in comparison to the reference control.

In some aspects, disclosed herein is a method of determining or predicting survival of a subject having low grade glioma (LGG), comprising:
  obtaining a biological sample derived from the subject having LGG;
  quantifying an expression level of a MAPT biomarker, a CASP9 biomarker, a UQCRC2 biomarker, or a combination thereof, in the biological sample derived from the subject having LGG; and
  determining or predicting the subject as having a survival of 59 months or less if the expression level of the MAPT biomarker, the CASP9 biomarker, the UQCRC2 biomarker, or the combination thereof, is lower in the biological sample derived from the subject compared to a reference control.

In some aspects, disclosed herein is a method of treating a subject having low grade glioma (LGG), comprising:
  obtaining a biological sample derived from the subject having LGG;
  quantifying an expression level of a MAPT biomarker, a CASP9 biomarker, a UQCRC2 biomarker, or a combination thereof, in the biological sample derived from the subject having LGG;
  determining or predicting the subject as having a survival of 59 months or less if the expression level of the MAPT biomarker, the CASP9 biomarker, the UQCRC2 biomarker, or the combination thereof, is lower in the biological sample derived from the subject compared to a reference control; and
  administering to the subject a therapeutically effective amount of an activator of MAPT, an activator of CASP9, an activator of UQCRC2, or a combination thereof.

In some embodiments, the expression level is a gene expression level. In some embodiments, the expression level is a protein expression level.

In addition to low grade glioma (LGG), the methods disclosed herein can also be used for determining or predicting survival of a subject having other brain cancers, spine tumors, or cancers of the nervous system (for example, neuroblastoma, including pediatric neuroblastoma) where lower levels of MAPT (Tau) are predictive of a shorter overall survival in comparison to a reference control. In some embodiments, the brain cancer is glioma (low grade glioma or high grade glioma). In some embodiments, the brain cancer is glioblastoma. In some embodiments, the brain cancer is anaplastic astrocytoma.

In some embodiments, the reference control is a healthy control. In some embodiments, the reference control is a non-cancerous control. In some embodiments, the reference control is from a patient without LGG. In some embodiments, the reference control is from a pooled population of patient samples or biological samples.

In one embodiment of the present disclosure, a kit is provided for determining or predicting the overall survival of a subject having low grade glioma (LGG), the kit comprising:
primers for quantifying a gene expression level of one or more biomarkers that are associated with overall survival in low grade glioma (LGG) in a biological sample derived from a subject relative to a reference control, wherein the primers are for one or more biomarkers comprising MAPT, CASP9, and UQCRC2; and
instructions for determining or predicting one of:
  a. the subject as having a shorter overall survival if the expression level of one or more of the biomarkers MAPT, CASP9, and UQCRC2 is lower in the biological sample derived from the subject compared to the reference control, or
  b. the subject as having a longer overall survival if the expression level of one or more of the biomarkers MAPT, CASP9, and UQCRC2 is higher in the biological sample derived from the subject compared to the reference control.

In other aspects, disclosed herein is a method of treating a subject having low grade glioma (LGG), comprising:
obtaining a biological sample derived from the subject having LGG;
quantifying an expression level of one or more biomarkers that are associated with overall survival in low grade glioma (LGG) in the biological sample derived from the subject relative to a reference control, wherein the biomarker comprises one or more of MAPT, CASP9, and UQCRC2;
determining or predicting the subject as having a shorter overall survival if the expression level of one or more of the biomarkers MAPT, CASP9, and UQCRC2 is lower in the biological sample derived from the subject compared to the reference control; and
administering to the subject a therapeutically effective amount of an appropriate LGG therapy.

In some embodiments, the appropriate LGG therapy comprises, for example, temozolomide (Temodar), bevacizumab (Avastin), Lomustine (CCNU, Ceenu), Carmustine wafer (BCNU, Gliadel), Afinitor (Everolimus), procarbazine, Vincristine (Onocovin), irinotecan, cordycepin, fenretinide, or combinations thereof. In some embodiments, the appropriate LGG therapy can also comprise surgery and/or radiation therapy.

In some aspects, disclosed herein is a method for determining or predicting the overall survival of a subject having low grade glioma (LGG), comprising:
obtaining a biological sample derived from the subject having LGG;
quantifying an expression level of one or more biomarkers that are associated with overall survival in LGG in the biological sample derived from the subject relative to a reference control, wherein the biomarker comprises one or more of H2AFX, HIST1H2BK, and HIST2H2BE; and
determining or predicting one of:
  a. the subject as having a shorter overall survival if the expression level of one or more of the biomarkers H2AFX, HIST1H2BK, and HIST2H2BE is higher in the biological sample derived from the subject compared to the reference control, or
  b. the subject as having a longer overall survival if the expression level of one or more of the biomarkers H2AFX, HIST1H2BK, and HIST2H2BE is lower in the biological sample derived from the subject compared to the reference control.

In some embodiments, the biomarker comprises H2AFX. In some embodiments, the biomarker comprises HIST1H2BK. In some embodiments, the biomarker comprises HIST2H2BE.

In some embodiments, the method further comprises: administering an inhibitor of H2AFX expression, an inhibitor of HIST1H2BK expression, an inhibitor of HIST2H2BE expression, or a combination thereof.

In other aspects, disclosed herein is a method of treating a subject having low grade glioma (LGG), comprising:
obtaining a biological sample derived from the subject having LGG;
quantifying an expression level of one or more biomarkers that are associated with overall survival in LGG in the biological sample derived from the subject relative to a reference control, wherein the biomarker comprises one or more of H2AFX, HIST1H2BK, and HIST2H2BE;
determining or predicting the subject as having a shorter overall survival if the expression level of one or more of the biomarkers H2AFX, HIST1H2BK, and HIST2H2BE is higher in the biological sample derived from the subject compared to the reference control; and
administering to the subject a therapeutically effective amount of an inhibitor of H2AFX expression, an inhibitor of HIST1H2BK expression, an inhibitor of HIST2H2BE expression, or a combination thereof.

In other aspects, disclosed herein is a method of treating a subject having low grade glioma (LGG), comprising:
obtaining a biological sample derived from the subject having LGG;
quantifying an expression level of one or more biomarkers that are associated with overall survival in LGG in the biological sample derived from the subject relative to a reference control, wherein the biomarker comprises one or more of H2AFX, HIST1H2BK, and HIST2H2BE;
determining or predicting the subject as having a shorter overall survival if the expression level of one or more of the biomarkers H2AFX, HIST1H2BK, and HIST2H2BE is higher in the biological sample derived from the subject compared to the reference control; and
administering to the subject a therapeutically effective amount of an appropriate LGG therapy.

In some aspects, disclosed herein is a method for determining or predicting the overall survival of a subject having pediatric neuroblastoma, comprising:
obtaining a biological sample derived from the subject having pediatric neuroblastoma;
quantifying an expression level of one or more biomarkers that are associated with overall survival in pediatric neuroblastoma in the biological sample derived from the subject relative to a reference control, wherein the biomarker comprises one or more of MAPT, CASP3, and CASP9; and determining or predicting one of:
a. the subject as having a shorter overall survival if the expression level of one or more of the biomarkers MAPT, CASP3, and CASP9 is lower in the biological sample derived from the subject compared to the reference control, or
b. the subject as having a longer overall survival if the expression level of one or more of the biomarkers MAPT, CASP3, and CASP9 is higher in the biological sample derived from the subject compared to the reference control.

In some embodiments, the biomarker comprises MAPT. In some embodiments, the biomarker comprises CASP3. In some embodiments, the biomarker comprises CASP9.

In some embodiments, the biological sample comprises one or a combination of tumor tissue, tumor cells, or biopsy tissue. In some embodiments, the biological sample comprises a blood sample.

In some embodiments, the quantifying is carried out to detect gene expression levels. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the quantifying is carried out to detect protein expression levels. In some embodiments, the quantifying is carried out by one or a combination of Western blot, ELISA, flow cytometry, immunohistochemistry, and other methods of detection using antibodies (for example, antibodies to recognize the MAPT (Tau), CASP3, or CASP9 biomarker proteins).

In some embodiments, the quantifying is carried out to detect gene methylation and gene copy number. For example, with low MAPT, there may be loss of DNA that is the cause of low MAPT, or methylation of the MAPT gene may reduce MAPT expression.

In some embodiments, the reference control is the expression level of the appropriate biomarker for the lowest quintile (20%) of the biomarker levels of a reference population of pediatric neuroblastoma patient samples. In some embodiments, the reference control is the expression level of the appropriate biomarker for the highest quintile (20%) of the biomarker levels of a reference population of pediatric neuroblastoma patient samples.

In some embodiments, the reference control is the expression level of the appropriate biomarker for the lowest 10%, 20%, 30%, 40%, or 50% of the biomarker levels of a reference population of pediatric neuroblastoma patient samples. In some embodiments, the reference control is the expression level of the appropriate biomarker for the highest 10%, 20%, 30%, 40%, or 50% of the biomarker levels of a reference population of pediatric neuroblastoma patient samples.

In some embodiments, the method further comprises administering an appropriate pediatric neuroblastoma therapy to the subject based on the prediction of the subject as having a shorter overall survival. In some embodiments, the method further comprises administering an appropriate pediatric neuroblastoma therapy to the subject based on the prediction of the subject as having an overall survival of 37 months or less.

In some embodiments, the method further comprises administering an appropriate pediatric neuroblastoma therapy to the subject based on the prediction of the subject as having an overall survival of about 20 months or less, about 25 months or less, about 30 months or less, about 35 months or less, about 40 months or less, about 45 months or less, about 50 months or less, about 55 months or less, about 60 months or less, about 65 months or less, about 70 months or less, about 75 months or less, about 80 months or less, about 85 months or less, about 90 months or less, about 95 months or less, or about 100 months or less.

In some embodiments, the method further comprises: administering an activator of MAPT, an activator of CASP3, an activator of CASP9, or a combination thereof. In some embodiments, the method further comprises: administering an activator of MAPT. In some embodiments, the activator of MAPT is cordycepin. In some embodiments, the activator of MAPT is a cordycepin derivative (see for example, U.S. Pat. Nos. 6,949,521 or 5,550,111). In some embodiments, the activator of MAPT is fenretinide.

Cordycepin is an adenosine analogue (3'-deoxyadenosine). In some embodiments, additional adenosine analogues or other nucleoside analogues can be used.

In some embodiments, the appropriate pediatric neuroblastoma therapy is administered in a therapeutically effective amount. In some embodiments, the activator of MAPT, the activator of CASP3, the activator of CASP9, or the combination thereof, is administered in a therapeutically effective amount.

In some embodiments, the pediatric neuroblastoma therapy can raise ceramide levels. Ceramides are known to raise tau levels and thus activators of ceramide levels can be used as activators of tau (for example, fenretinide or see U.S. Pat. No. 8,143,313). In some embodiments, the LGG therapy can include compounds that are microtubule stabilizing agents, as tau is known to stabilize microtubules (for example, paclitaxel or docetaxel).

In some embodiments, the subject is a human.

In some aspects, disclosed herein is a method for determining or predicting the overall survival of a subject having pediatric neuroblastoma, comprising:
quantifying an expression level of one or more biomarkers that are associated with overall survival in pediatric neuroblastoma in the biological sample derived from the subject relative to a reference control, wherein the biomarker comprises one or more of MAPT, CASP3, and CASP9; and determining or predicting one of:
a. the subject as having a shorter overall survival if the expression level of one or more of the biomarkers MAPT, CASP3, and CASP9 is lower in the biological sample derived from the subject compared to the reference control, or
b. the subject as having a longer overall survival if the expression level of one or more of the biomarkers MAPT, CASP3, and CASP9 is higher in the biological sample derived from the subject compared to the reference control.

In some aspects, disclosed herein is a method for determining or predicting the disease-free survival of a subject having pediatric neuroblastoma, comprising:
obtaining a biological sample derived from the subject having pediatric neuroblastoma;
quantifying an expression level of one or more biomarkers that are associated with disease-free survival in pediatric neuroblastoma in the biological sample derived from the subject relative to a reference control, wherein the biomarker comprises one or more of MAPT, CASP3, and CASP9; and determining or predicting one of:
  a. the subject as having a shorter disease-free survival if the expression level of one or more of the biomarkers MAPT, MAPT, CASP3, and CASP9 is lower in the biological sample derived from the subject compared to the reference control, or
  b. the subject as having a longer disease-free survival if the expression level of one or more of the biomarkers MAPT, CASP3, and CASP9 is higher in the biological sample derived from the subject compared to the reference control.

In other aspects, disclosed herein is a method of treating a subject having pediatric neuroblastoma, comprising:
obtaining a biological sample derived from the subject having pediatric neuroblastoma;
quantifying an expression level of one or more biomarkers that are associated with overall survival in pediatric neuroblastoma in the biological sample derived from the subject relative to a reference control, wherein the biomarker comprises one or more of MAPT, CASP3, and CASP9;
determining or predicting the subject as having a shorter overall survival if the expression level of one or more of the biomarkers MAPT, CASP3, and CASP9 is lower in the biological sample derived from the subject compared to the reference control; and
administering to the subject a therapeutically effective amount of an activator of MAPT, an activator of CASP3, an activator of CASP9, or a combination thereof.

In some embodiments, the biomarker comprises MAPT. In some embodiments, the biomarker comprises CASP3. In some embodiments, the biomarker comprises CASP9.

In some embodiments, the biological sample comprises one or a combination of tumor tissue, tumor cells, or biopsy tissue. In some embodiments, the biological sample comprises a blood sample.

In some embodiments, the quantifying is carried out to detect gene expression levels. In some embodiments, the quantifying is carried out by one or a combination of Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

In some embodiments, the quantifying is carried out to detect protein expression levels. In some embodiments, the quantifying is carried out by one or a combination of Western blot, ELISA, flow cytometry, and other methods of detection using antibodies (for example, antibodies to recognize the MAPT (Tau), CASP3, and CASP9 biomarker proteins).

In some embodiments, the reference control is the expression level of the appropriate biomarker for the lowest quintile (20%) of the biomarker levels of a reference population of pediatric neuroblastoma patient samples. In some embodiments, the reference control is the expression level of the appropriate biomarker for the highest quintile (20%) of the biomarker levels of a reference population of pediatric neuroblastoma patient samples.

In some embodiments, the method further comprises administering an appropriate pediatric neuroblastoma therapy to the subject based on the prediction of the subject as having a shorter overall survival. In some embodiments, the method further comprises administering an appropriate pediatric neuroblastoma therapy to the subject based on the prediction of the subject as having an overall survival of 37 months or less. In some embodiments, the method further comprises administering a differing amount of appropriate pediatric neuroblastoma therapy to a patient based on the level of biomarker expression (MAPT (Tau), CASP3, and CASP9 biomarkers). For example, patients with relatively lower levels of MAPT (Tau) expression would be administered higher amounts of pediatric neuroblastoma therapy (for example, cordycepin), while patients with relatively higher levels of expression of MAPT (Tau) expression would be administered lower amounts of pediatric neuroblastoma therapy (for example, cordycepin).

In some embodiments, the method further comprises: administering an activator of MAPT, an activator of CASP3, an activator of CASP9, or a combination thereof. In some embodiments, the method further comprises: administering an activator of MAPT. In some embodiments, the activator of MAPT is cordycepin. In some embodiments, the activator of MAPT is a cordycepin derivative (see for example, U.S. Pat. Nos. 6,949,521 or 5,550,111). In some embodiments, the activator of MAPT is fenretinide.

In some embodiments, the subject is a human.

In other aspects, disclosed herein is a method of treating a subject having pediatric neuroblastoma, comprising:
quantifying an expression level of one or more biomarkers that are associated with overall survival in pediatric neuroblastoma in the biological sample derived from the subject relative to a reference control, wherein the biomarker comprises one or more of MAPT, CASP3, and CASP9;
determining or predicting the subject as having a shorter overall survival if the expression level of one or more of the biomarkers MAPT, CASP3, and CASP9 is lower in the biological sample derived from the subject compared to the reference control; and
administering to the subject a therapeutically effective amount of an activator of MAPT, an activator of CASP3, an activator of CASP9, or a combination thereof.

In some embodiments, the biomarker comprises MAPT. In some embodiments, the biomarker comprises CASP3. In some embodiments, the biomarker comprises CASP9.

In some embodiments, the level of the one or more of the biomarkers MAPT, CASP3, and CASP9 determines the subject as having a 10% or more (for example 10% or more, 20% or more, 30% or more, 40% or more, 50% or more, 60% or more, 70% or more, 80% or more, 90% or more, 100% or more) increase in survival in comparison to the reference control.

In some aspects, disclosed herein is a method of determining or predicting survival of a subject having pediatric neuroblastoma, comprising:
  obtaining a biological sample derived from the subject having pediatric neuroblastoma;
  quantifying an expression level of a MAPT biomarker, a CASP3 biomarker, a CASP9 biomarker, or a combination thereof, in the biological sample derived from the subject having pediatric neuroblastoma; and
  determining or predicting the subject as having a survival of 37 months or less if the expression level of the MAPT biomarker, the CASP3 biomarker, the CASP9 biomarker, or the combination thereof, is lower in the biological sample derived from the subject compared to a reference control.

In some aspects, disclosed herein is a method of treating a subject having pediatric neuroblastoma, comprising:
  obtaining a biological sample derived from the subject having pediatric neuroblastoma;
  quantifying an expression level of a MAPT biomarker, a CASP3 biomarker, a CASP9 biomarker, or a combination thereof, in the biological sample derived from the subject having pediatric neuroblastoma;

determining or predicting the subject as having a survival of 37 months or less if the expression level of the MAPT biomarker, the CASP3 biomarker, the CASP9 biomarker, or the combination thereof, is lower in the biological sample derived from the subject compared to a reference control; and administering to the subject a therapeutically effective amount of an activator of MAPT, an activator of CASP3, an activator of CASP9, or a combination thereof.

In some embodiments, the expression level is a gene expression level. In some embodiments, the expression level is a protein expression level.

In some embodiments, the reference control is a healthy control. In some embodiments, the reference control is a non-cancerous control. In some embodiments, the reference control is from a patient without pediatric neuroblastoma. In some embodiments, the reference control is from a pooled population of patient samples or biological samples.

In one embodiment of the present disclosure, a kit is provided for determining or predicting the overall survival of a subject having pediatric neuroblastoma, the kit comprising:

primers for quantifying a gene expression level of one or more biomarkers that are associated with overall survival in pediatric neuroblastoma in a biological sample derived from a subject relative to a reference control, wherein the primers are for one or more biomarkers comprising MAPT, CASP3, and CASP9; and instructions for determining or predicting one of:
 a. the subject as having a shorter overall survival if the expression level of one or more of the biomarkers MAPT, CASP3, and CASP9 is lower in the biological sample derived from the subject compared to the reference control, or
 b. the subject as having a longer overall survival if the expression level of one or more of the biomarkers MAPT, CASP3, and CASP9 is higher in the biological sample derived from the subject compared to the reference control.

In some aspects, disclosed herein is a method for determining or predicting the overall survival of a subject having pediatric neuroblastoma, comprising:

obtaining a biological sample derived from the subject having pediatric neuroblastoma;

quantifying an expression level of one or more biomarkers that are associated with overall survival in pediatric neuroblastoma in the biological sample derived from the subject relative to a reference control, wherein the biomarker comprises one or more of H1FX and HIST2H3D; and determining or predicting one of:
 a. the subject as having a shorter overall survival if the expression level of one or more of the biomarkers H1FX and HIST2H3D is higher in the biological sample derived from the subject compared to the reference control, or
 b. the subject as having a longer overall survival if the expression level of one or more of the biomarkers H1FX and HIST2H3D is lower in the biological sample derived from the subject compared to the reference control.

In some embodiments, the biomarker comprises H1FX. In some embodiments, the biomarker comprises HIST2H3D.

In some embodiments, the method further comprises: administering an inhibitor of H1FX expression, an inhibitor of HIST2H3D expression, or a combination thereof.

In other aspects, disclosed herein is a method of treating a subject having pediatric neuroblastoma, comprising:

obtaining a biological sample derived from the subject having pediatric neuroblastoma;

quantifying an expression level of one or more biomarkers that are associated with overall survival in pediatric neuroblastoma in the biological sample derived from the subject relative to a reference control, wherein the biomarker comprises one or more of H1FX and HIST2H3D;

determining or predicting the subject as having a shorter overall survival if the expression level of one or more of the biomarkers H1FX and HIST2H3D is higher in the biological sample derived from the subject compared to the reference control; and administering to the subject a therapeutically effective amount of an inhibitor of H1FX expression, an inhibitor of HIST2H3D expression, or a combination thereof.

In other aspects, disclosed herein is a method of treating a subject having pediatric neuroblastoma, comprising:

obtaining a biological sample derived from the subject having pediatric neuroblastoma;

quantifying an expression level of one or more biomarkers that are associated with overall survival in pediatric neuroblastoma in the biological sample derived from the subject relative to a reference control, wherein the biomarker comprises one or more of H1FX and HIST2H3D;

determining or predicting the subject as having a shorter overall survival if the expression level of one or more of the biomarkers H1FX and HIST2H3D is higher in the biological sample derived from the subject compared to the reference control; and administering to the subject a therapeutically effective amount of an appropriate pediatric neuroblastoma therapy.

In other aspects, disclosed herein is a method of treating a subject having pediatric neuroblastoma, comprising:

obtaining a biological sample derived from the subject having pediatric neuroblastoma;

quantifying an expression level of one or more biomarkers that are associated with overall survival in pediatric neuroblastoma in the biological sample derived from the subject relative to a reference control, wherein the biomarker comprises one or more of MAPT, CASP3, and CASP9;

determining or predicting the subject as having a shorter overall survival if the expression level of one or more of the biomarkers MAPT, CASP3, and CASP9 is lower in the biological sample derived from the subject compared to the reference control; and administering to the subject a therapeutically effective amount of an appropriate pediatric neuroblastoma therapy.

In some embodiments, the appropriate pediatric neuroblastoma therapy comprises, for example, Fenretinide, Cyclophosphamide, Dinutuximab, Doxorubicin Hydrochloride, Unituxin (Dinutuximab), Unituxin (Dinutuximab), Vincristine Sulfate, Busulfan, Melphalan Hydrochloride, Carboplatin, Etoposide Phosphate, cordycepin or a combination thereof.

In some embodiments, in addition to the above listed chemotherapeutic agents, additional chemotherapeutic agents can also be administered to a subject. Additional chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antis, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorubicin citrate, denileukin diftitox, Dexrazoxane, Dibromomannitol, dihydroxy anthracin dione, Docetaxel, dolasetron mesylate, doxorubicin HCL, dronabinol, $E.\ coli$ L-asparaginase, emetine, epoetin-α, Envinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional chemotherapeutic agents or therapeutic agents that can be administered in combination with the compounds disclosed herein can also include bevacizumab, sutinib, sorafenib, 2-methoxyestradiol, finasunate, vatalanib, vandetanib, aflibercept, volociximab, etaracizumab, cilengitide, erlotinib, cetuximab, panitumumab, gefitinib, trastuzumab, atacicept, rituximab, alemtuzumab, aldesleukine, atlizumab, tocilizumab, temsirolimus, everolimus, lucatumumab, dacetuzumab, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, oblimersen, plitidepsin, talmapimod, enzastaurin, tipifarnib, perifosine, imatinib, dasatinib, lenalidomide, thalidomide, simvastatin, and celecoxib.

Nomenclature abbreviations for genes and proteins can be found in the HUGO database, where the sequences for the RNA, RNA, and proteins can be found. For example: MAPT, HGNC:6893; CASP9, HGNC:1511; UQCRC2, HGNC:12586; CASP3, HGNC:1504v; H1FX, HGNC:4722; HIST2H3D, HGNC:25311; H2AFX, HGNC:4739; HIST1H2BK, HGNC:13954; HIST2H2BE, HGNC:4760.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. MAPT (Tau) Expression is a Biomarker for an Increased Rate of Survival for Low-Grade Glioma The association of MAPT (Tau) with various tauopathies and other neurological disorders has long been established. However, the role of MAPT expression in brain cancer is largely unknown. To determine whether MAPT expression is related to low-grade glioma (LGG) survival rates, RNASeq data representing samples from the cancer genome atlas (TCGA) were assessed. Results revealed that high expression of the MAPT gene is very strongly associated with increased overall and disease free survival in LGG but not in breast cancer or melanoma. No such association was apparent for either amyloid precursor protein or α-synuclein gene expression. The expression levels of particular apoptosis- and pro-proliferative effector genes were consistent with the tau-associated increased, survival rates. It has been well established that the tau protein plays a neurodegenerative role, and in this report, for the first time, a cell apoptosis function for tau is identified.

1. BACKGROUND

The MAPT gene (Microtubule Associated Protein—Tau) encodes the tau protein, which is involved in microtubule stabilization and tubulin polymerization into microtubules. It has long been established that aggregations of hyperphosphorylated neurofibrillary and gliofibrillary tangles of tau protein are involved in several neurodegenerative disorders, known as tauopathies [1, 2]. However, the role of tau in brain cancers, and specifically, low-grade glioma, has not been explored.

Gliomas are histologically graded from I to IV. Grade I gliomas are usually benign. Grade II (Low Grade Glioma (LGG)) has an average survival period of approximately 7 years. Grade II gliomas can progress into grade III (high grade gliomas), and eventually grade IV (secondary glioblastoma). Recent research indicates that historically used clinical variables in LGG are inferior prognostic indicators relative to current genetic information, for example IDH1 mutational status [3]. As LGG is an early stage in the progression of gliomas from low grade to high grade, there is a need to understand the disease process from this early onset. Pinpointing key molecular features that are associated with improved outcomes will help elucidate the disease progression and serve as prognostic markers in the clinic [4].

Given tau's role in neurodegeneration in the brain and microtubule stabilization, it was of interest to explore tau's connection to LGG. Colodner et al. have demonstrated that glial fibrillary tangle formation was accompanied by JAK/STAT-mediated apoptotic cell death of both glia and neurons in a *drosophila* model of glial tauopathy [5]. However, previous research on tau in the cancer setting, for the most part, has focused on microtubule-inhibiting chemotherapy in breast cancer [6-8]. For example, Zhou et al. have identified tau expression as a factor to predict tumor sensitivity to microtubule-inhibiting compounds such as taxanes [9]. In the present example, the association of tau with the survival of LGG patients was investigated.

2. METHODS

2.1 MAPT, Apoptosis-Effector Gene and Pro-Proliferative Gene RNAseq Analysis.

RNASeq values for MAPT, for the panel of apoptosis-effector genes, and for the panel of pro-proliferative genes, were downloaded from cBioPortal.org. Pearson correlation coefficients were obtained, using Microsoft Excel [10-12].

2.2 Kaplan Meier Analyses and RNAseq Data

The barcodes (patients identifiers) representing 530 LGG samples, 1105 BRCA samples, and 478 SKCM samples, for which RNASeq data were available, were sorted from low to high based on the RNASeq values for each of the indicated genes in Results. Survival relationships were then obtained by matching barcode survival data, available from cbioportal.org, with the RNASeq data representing the top and bottom 20% of the RNASeq values (106 barcodes for LGG, 221 barcodes for BRCA, and 94 barcodes for SKCM); and with the top and bottom 50%, 40%, 30% and 10% of the RNASeq values for MAPT (LGG only). The clinical data (months of overall survival and disease free survival) for the associated barcodes were then processed using IBM Statistics Package for the Social Sciences (SPSS), version 24, to provide the KM curves and an average difference in survival rates between samples representing the top and bottom RNASeq value percentages (for the genes as indicated in Results).

2.3 Histological Grade Analysis

Histological grades for LGG barcodes were downloaded from cBioPortal.org. Histological grades were then matched to barcode RNAseq data (106 barcodes for LGG). Comparison of proportions test between data representing the top and bottom 20% of the MAPT RNASeq values was done using the Medcalc comparison of proportions calculator (https://www.medcalc.org/calc/comparison_of_proportions.php).

2.4 Copy Number Variation (CNV) Analysis

Copy numbers for the MAPT gene for LGG barcodes were downloaded from cBioPortal.org. Copy numbers were then matched to barcode RNAseq data (530 barcodes for LGG). A Student's T-test between copy number data representing the top and bottom 20% of the MAPT RNASeq values was done using the Microsoft Excel function.

2.5 Methylation Analysis

Methylation data for the MAPT gene for LGG barcodes were downloaded from cBioPortal.org. Methylation data were then matched to barcode RNAseq data (530 barcodes for LGG). A Student's T-test between methylation data representing the top and bottom 20% of the MAPT RNASeq values was done using the Microsoft Excel function.

2.6 Diagnosis Age Analysis

Diagnosis age data for LGG barcodes were downloaded from cBioPortal.org. Diagnosis ages were then matched to barcode RNAseq data (530 barcodes for LGG). A Student's T-test between diagnosis age representing the top and bottom 20% of the MAPT RNASeq values was done using the Microsoft excel function.

2.7. R2: Genomics Analysis and Visualization Platform.

MAPT gene expression and overall survival data for additional glioma datasets were assessed using the 'R2: Genomics Analysis and Visualization Platform (http://r2.amc.nl)'. Single gene Kaplan scan analysis was conducted for MAPT expression (203929_s_at) for each dataset as indicated in Results. Median MAPT mRNA expression was used as a cutoff for overall survival comparisons. The R2 algorithm was used to generate Kaplan-Meier analyses to compare survival outcomes for the top half versus bottom half of MAPT expressers in each indicated dataset.

3. RESULTS

3.1 MAPT (Tau) Expression and Survival Rates

First, the rate of overall and disease free survival for LGG patients representing the top and bottom 20% of MAPT expressers was compared, based on the MAPT RNASeq values representing the TCGA-LGG data set (FIG. 1). This comparison indicates that high MAPT RNASeq values are associated with a significantly increased overall and disease free survival rates for LGG. To substantiate this result, the top 10%, 30%, 40% and 50% MAPT expressers were compared with their corresponding lower level MAPT expressers for overall survival. In all cases, the initial result was confirmed: top 30% of MAPT expressers, compared to the OS for the bottom 30% of MAPT expressers was 104.107 months vs. 73.895 months, respectively; top 40% of MAPT expressers, compared to the OS for the bottom 40% of MAPT expressers was 102.784 months vs. 87.106 months, respectively; top 50% of MAPT expressers, compared to the OS for the bottom 50% of MAPT expressers was 104.839 months vs. 83.912 months, respectively.

To determine whether the above association of MAPT RNASeq levels with the dramatically distinct survival rates was specific to LGG, data for overall survival and disease free survival for BRCA and SKCM tumor barcodes were downloaded from cBioPortal.org, and the RNAseq and KM analyses were conducted. Results indicated that MAPT expression levels did not correlate with either overall or disease free survival rate differences in the cases of BRCA or SKCM (FIG. 1). The mean survival periods and p-values for the log-rank tests are given in the figure legend for FIG. 1. These data indicate that the higher overall and disease free survival rates for high MAPT expressing patients is specific to LGG.

Figure 2A:
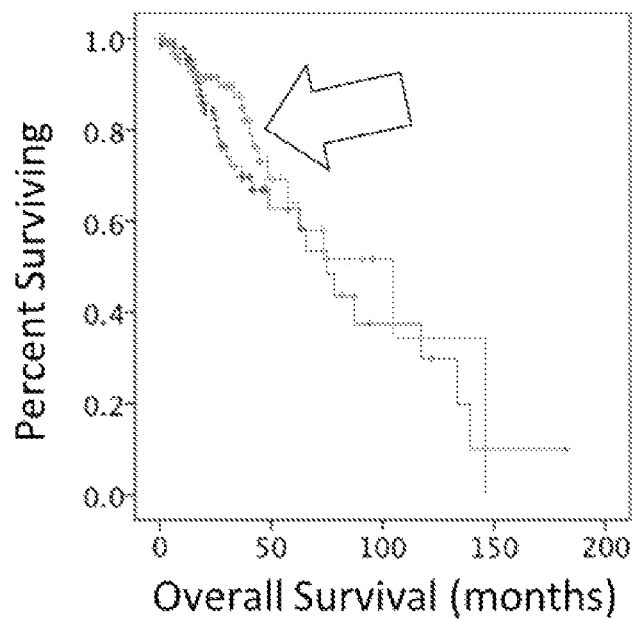
FIGS. 2A-2B. Kaplan-Meier curves representing distinct APP and SNCA expression levels. Results here indicated that no survival distinctions are detectable for LGG based on APP or SNCA expression levels.
Figure 2B:
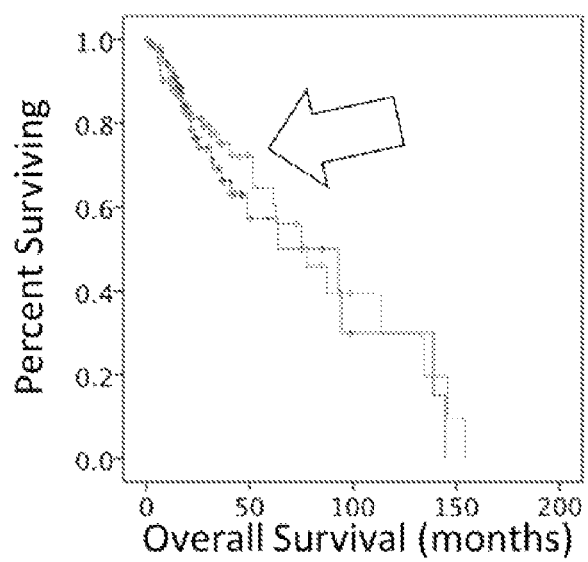

To determine whether the increased LGG survival rate associated with MAPT expression could be associated with other neurotoxic proteins, it was assessed whether significantly increased survival rates could be associated with higher RNASeq values for APP or SNCA. Analyses indicated there were no differences in survival for the patients represented by the LGG barcodes representing the top and bottom quintiles, for RNASeq values for APP or SNCA, respectively (FIG. 2).

3.2 LGG Apoptosis-Effector Gene RNASeq Values Correlated with MAPT RNASeq Values As tau is a neurotoxic protein associated with various tauopathies, and contributing to neuronal cell death, the inventors then determined whether apoptosis-effector genes were expressed at higher levels in the LGG samples represented by the barcodes with higher levels of MAPT RNAseq values. A set of 28 apoptosis effector genes [13] was evaluated for RNAseq expression as represented by the LGG barcodes. Of those 28 genes, a subset of five apoptosis-effector genes was identified that had significantly increased RNASeq values associated with barcodes that represented the top 20% of MAPT expressors: CASP9, CYC1, CRADD, COX7A2L, and UQCRC2 (Table 1).

To verify the above positive correlations of apoptosis-effector gene RNASeq values with MAPT RNASeq values, the Pearson correlation coefficients were obtained for the MAPT RNA expression levels and the RNA expression levels of CASP9, CYC1, CRADD, COX7A2L and UQCRC2 in LGG. In each case, there was a statistically significant correlation with MAPT expression (FIG. 3).

Figure 4A:
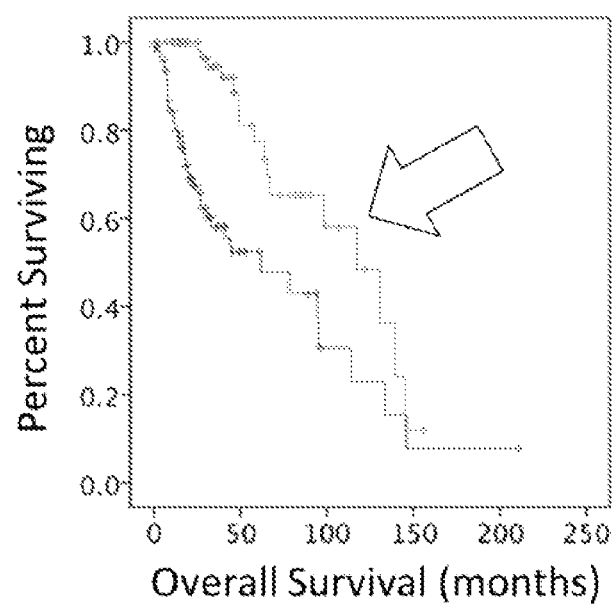
FIGS. 4A-4B. Kaplan-Meier curves representing distinct apoptosis-effector gene expression levels. Results presented here indicated that apoptosis-effector gene expression represented an independent marker of survival rates.
Figure 4B:
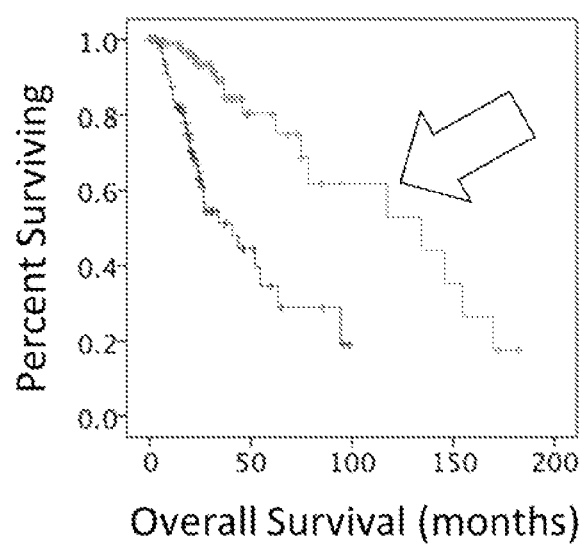

To determine whether any of the five above identified apoptosis-effector genes could represent independent markers of survival rates, the overall survival data for LGG barcodes representing the highest 20% and lowest 20% of CASP9, CYC1, CRADD, COX7A2L and UQCRC2 expression levels were obtained for KM analysis. Results indicated that only CASP9 and UQCRC2 represented independent markers of survival, with barcodes representing the highest 20% of both CASP9 and UQCRC2 having significantly increased survival rates (FIG. 4).

3.3 LGG Proliferation-Effector Gene RNASeq Values Correlated with MAPT RNASeq Values The inventors next sought to determine whether any proliferation effector genes were expressed at higher levels in the samples with lower levels of the MAPT RNAseq values. A panel of 62 proliferation effector genes was investigated [13]. Of those 62 genes, a subset of 25 proliferation-effector genes were identified that have significantly increased RNASeq expression in barcodes that represent the bottom 20% of MAPT expressers.

To verify the above inverse correlations of proliferation-effector gene expression with MAPT expression, the Pearson correlation coefficients were obtained for MAPT RNASeq values and the RNASeq values for a histone subset of the above indicated, 28 proliferation-effector genes, for the LGG barcodes: H2AFX, HIST1H2BK and HIST2H2BE. In each case, there was a statistically significant inverse correlation with MAPT expression (FIG. 5).

To determine where any of the above indicated histone genes represented independent survival markers, KM survival curves were generated based on the top and bottom LGG expressers. From these analyses, it was determined that the expression of all three of the histone genes independently represented survival distinctions (Table 2).

3.4 LGG Histological Grade Correlated with MAPT RNASeq Values

To determine whether MAPT expression correlates with histological features of LGG, histological grades of the top quintile and bottom quintile of MAPT expressing barcodes were compared. All LGG barcodes in the dataset used were graded either G2 or G3. It was determined that the low MAPT-expressing barcodes, that also represented decreased survival rates, also had a greater proportion of G3 histological grade than the high MAPT-expressing barcodes (Table 3).

3.5 CNV and Methylation Correlated with MAPT RNASeq Values in LGG

To determine whether there may be any genetic or epigenetic associations with increased MAPT expression, MAPT copy number variation and methylation of the MAPT gene was compared in the top quintile and bottom quintile of MAPT expressing barcodes using data available on cBioPortal.org. For CNV, a negative result indicates average copy number loss, while a positive result indicates average copy number gain among the barcodes analyzed. These results indicate that there is an average increase in MAPT copy number among barcodes that are in the top quintile of MAPT expressers, while there is an average decrease in copy number among barcodes that are in the bottom quintile of MAPT expressers. Furthermore, these results indicate that there is an increase in MAPT gene methylation among barcodes that are in the bottom quintile of MAPT expressers (Table 4). Together, the CNV and methylation results indicate that there are likely genetic and epigenetic explanations for decreased MAPT expression.

3.6 Diagnosis Age Correlated with MAPT RNASeq Values in LGG

To determine whether MAPT expression may have an effect on diagnosis age, the average age of diagnosis was compared in patient barcodes representing the top and bottom quintile of MAPT RNAseq expression using data available on cBioPortal.org. Results indicated that increased MAPT expression was associated with an earlier diagnosis age. The top quintile of MAPT expressers had an average diagnosis age of 39, while the lowest quintile of MAPT expressers had an average diagnosis age of 48 (Table 5).

3.7 Analysis of MAPT Expression and Survival in Additional Glioma Datasets from the R2: Genomics Analysis and Visualization Platform.

To determine if MAPT mRNA expression is associated with improved survival outcomes in additional, independent glioma datasets, the R2: Genomics analysis and visualization platform was used. Two additional glioma datasets were analyzed, French (n=284) and Kawaguchi (n=50). In both datasets, the top half of MAPT expressers had improved overall survival outcomes when compared to the bottom half of MAPT expressers (Table 6). Thus, results from these datasets were consistent with the above analyses of the TCGA LGG dataset.

DISCUSSION

In sum, the above data and analyses indicate that tau expression is associated with a dramatic increase in survival in LGG patients. While the tau mechanism in LGG is unknown, it was demonstrated that increased tau expression was correlated with an increase in the expression of several apoptosis-effector genes; and that lack of tau was associated with a higher level of proliferation-effector gene expression. Also, the histological grade of the tumor inversely correlated with tau expression.

The precise question of tau-induced neurotoxicity in the tauopathies also remains a mystery, but may be due to multiple causes, including DNA damage. In neurons, tau aggregates become misfolded and hyper-phosphorylated, leading to the bundling and stabilization of filamentous actin, ultimately causing oxidative stress in the cell through dysfunctional mitochondria. The oxidative stress causes DNA damage and causes the loss of heterochromatin, allowing genes that are normally silenced by heterochromatin to be transcribed, ultimately leading to cell cycle activation and apoptosis in mature neurons [14]. Several studies have noted the link between DNA damage and neurodegeneration in Alzheimer's disease [15-19].

While much has been explored regarding the role of tau pathology in neurons, there has been less focus on investigating the role of tau aggregation in glial cells. Several studies have demonstrated the functional consequences of tau aggregation in glial cells [5, 20]. Some studies indicate that tau pathology in glial cells is similar to that in neurons, to an extent, but is not identical [21, 22]. As shown in the present example, these results show that there is an increased expression of several apoptosis-effector genes in the population of patients that have high MAPT expression.

TABLE 1

Average apoptosis-effector gene RNASeq values for LGG barcodes representing high and low expression of MAPT

| Apoptosis Effector Gene | Bottom 20% MAPT RNASeq values | Top 20% MAPT RNASeq values | p-value |
|---|---|---|---|
| CASP9 | 511.0 | 901.2 | <0.0001 |
| COX7A2L | 1158.2 | 1300.2 | 0.0011 |
| CRADD | 193.1 | 215.0 | 0.0054 |
| CYC1 | 1952.8 | 2339.4 | <0.0001 |
| UQCRC2 | 2601.8 | 3853.1 | <0.0001 |

TABLE 2

Identifying proliferation-effector gene survival associations in LGG.

| Survival distinctions | Gene | | |
|---|---|---|---|
| | H2AFX | HIST1H2BK | HIST2H2BE |
| Increased/Decreased Survival for the top quintile of expressers of the indicated gene | Decreased | Decreased | Decreased |
| Increased/Decreased Survival for the bottom quintile of expressers of the indicated gene | Increased | Increased | Increased |
| KM, log-rank p-value | <0.0001 | <0.0001 | <0.0001 |

TABLE 3

Identifying histological grade associations with MAPT expression

| | Bottom quintile MAPT expressers | Top quintile MAPT expressers | p-value |
|---|---|---|---|
| Fraction G3 histological grade | 0.78 | 0.22 | <0.0001 |

TABLE 4

Copy number variation and methylation associations with MAPT expression

| | Bottom quintile MAPT expressers | Top quintile MAPT expressers | p-value |
|---|---|---|---|
| Copy Number Variation | −0.031 | 0.048 | 0.0002 |
| Methylation | 0.490 | 0.355 | 3.479E−13 |

TABLE 5

Diagnosis age associations with MAPT expression

| | Bottom quintile MAPT expressers | Top quintile MAPT expressers | p-value |
|---|---|---|---|
| Average age of diagnosis | 48.56 | 39.38 | 4.248E−07 |

TABLE 6

Identifying MAPT expression associations with survival in additional glioma datasets, using the R2: Genomics Analysis and Visualization Platform.

| Survival distinctions | Dataset | |
|---|---|---|
| | Glioma (French) n = 284 | Glioma (Kawaguchi) n = 50 |
| Increased/Decreased Survival for the top half of MAPT expressers in the indicated dataset | Increased | Increased |
| Increased/Decreased Survival for the bottom half of MAPT expressers in the indicated dataset | Decreased | Decreased |
| KM, log-rank p-value | <0.0001 | <0.001 |

Abbreviations

APP, Amyloid Precursor Protein gene; BRCA, breast cancer; CASP9, Caspase 9 gene; H2AFX, H2A histone family, member X gene; HIST1H2AL, Histone H2A type 1 gene; HIST1H2BK, Histone H2B type 1-K gene; HIST1H3J, Histone H3J gene; HIST1H4B, Histone H4B gene; HIST2H2BE, Histone H2B type 2-E gene; HUGO, human genome organization; KM, Kaplan-Meier survival curve; LGG, lower grade glioma; MAPT, microtubule associated protein, tau; gene symbol; SKCM, skin cutaneous, melanoma; SNCA, alpha-synuclein gene; SPSS, IBM Statistical Package for the Social Sciences; TCGA, the cancer genome atlas.

REFERENCES CITED IN THIS EXAMPLE

1. Spillantini M G, Goedert M (2013) Tau pathology and neurodegeneration. Lancet Neurol 12: 609-622 doi: 10.1016/S1474-4422(13) 70090-5
2. Ikeda K, Akiyama H, Arai T, Nishimura T (1998) Glial tau pathology in neurodegenerative diseases: their nature and comparison with neuronal tangles. Neurobiol Aging 19: S85-91
3. Hartmann C, Hentschel B, Tatagiba M, Schramm J, Schnell O, Seidel C, Stein R, Reifenberger G, Pietsch T, von Deimling A, Loeffler M, Weller M, German Glioma N (2011) Molecular markers in low-grade gliomas: predictive or prognostic? Clinical cancer research: an official journal of the American Association for Cancer Research 17: 4588-4599 doi:10.1158/1078-0432.CCR-10-3194
4. Claus E B, Walsh K M, Wiencke J K, Molinaro A M, Wiemels J L, Schildkraut J M, Bondy M L, Berger M, Jenkins R, Wrensch M (2015) Survival and low-grade glioma: the emergence of genetic information. Neurosurg Focus 38: E6 doi:10.3171/2014.10.FOCUS12367
5. Colodner K J, Feany M B (2010) Glial fibrillary tangles and JAK/STAT-mediated glial and neuronal cell death in a *Drosophila* model of glial tauopathy. J Neurosci 30: 16102-16113 doi:10.1523/JNEUROSCI.2491-10.2010
6. Li Z H, Xiong Q Y, Tu J H, Gong Y, Qiu W, Zhang H Q, Wei W S, Hou Y F, Cui W Q (2013) Tau proteins expressions in advanced breast cancer and its significance in taxane-containing neoadjuvant chemotherapy. Medical oncology 30: 591 doi:10.1007/s12032-013-0591-y
7. Koo D H, Lee H J, Ahn J H, Yoon D H, Kim S B, Gong G, Son B H, Ahn S H, Jung K H (2015) Tau and PTEN status as predictive markers for response to trastuzumab and paclitaxel in patients with HER2-positive breast cancer. Tumour biology: the journal of the International Society for Oncodevelopmental Biology and Medicine 36: 5865-5871 doi:10.1007/s13277-015-3258-9
8. Wang K, Deng Q T, Liao N, Zhang G C, Liu Y H, Xu F P, Zu J, Li X R, Wu Y L (2013) Tau expression correlated with breast cancer sensitivity to taxanes-based neoadjuvant chemotherapy. Tumour biology: the journal of the International Society for Oncodevelopmental Biology and Medicine 34: 33-38 doi:10.1007/s13277-012-0507-z
9. Zhou J, Qian S, Li H, He W, Tan X, Zhang Q, Han G, Chen G, Luo R (2015) Predictive value of microtubule-associated protein Tau in patients with recurrent and metastatic breast cancer treated with taxane-containing palliative chemotherapy. Tumour biology: the journal of the International Society for Oncodevelopmental Biology and Medicine 36: 3941-3947 doi:10.1007/s13277-015-3037-7
10. Grossman R L, Heath A P, Ferretti V, Varmus H E, Lowy D R, Kibbe W A, Staudt L M (2016) Toward a Shared Vision for Cancer Genomic Data. The New England journal of medicine 375: 1109-1112 doi:10.1056/NEJMp1607591
11. Gao J, Aksoy B A, Dogrusoz U, Dresdner G, Gross B, Sumer S O, Sun Y, Jacobsen A, Sinha R, Larsson E, Cerami E, Sander C, Schultz N (2013) Integrative analysis of complex cancer genomics and clinical profiles using the cBioPortal. Science signaling 6: pll doi:10.1126/scisignal.2004088
12. Ping Z, Siegal G P, Almeida J S, Schnitt S J, Shen D (2014) Mining genome sequencing data to identify the genomic features linked to breast cancer histopathology. Journal of pathology informatics 5: 3 doi:10.4103/2153-3539.126147
13. Mauro J A, Blanck G (2014) Functionally distinct gene classes as bigger or smaller transcription factor traps: a possible stochastic component to sequential gene expression programs in cancer. Gene 536: 398-406 doi:10.1016/j.gene.2013.11.013
14. Frost B, Gotz J, Feany M B (2015) Connecting the dots between tau dysfunction and neurodegeneration. Trends Cell Biol 25: 46-53 doi:10.1016/j.tcb.2014.07.005
15. Iijima-Ando K, Zhao L, Gatt A, Shenton C, Iijima K (2010) A DNA damage-activated checkpoint kinase phosphorylates tau and enhances tau-induced neurodegeneration. Hum Mol Genet 19: 1930-1938 doi:10.1093/hmg/ddq068
16. Khurana V, Merlo P, DuBoff B, Fulga T A, Sharp K A, Campbell S D, Gotz J, Feany M B (2012) A neuroprotective role for the DNA damage checkpoint in tauopathy. Aging Cell 11: 360-362 doi:10.1111/j.1474-9726.2011.00778.x
17. Kruman, I I, Wersto R P, Cardozo-Pelaez F, Smilenov L, Chan S L, Chrest F J, Emokpae R, Jr., Gorospe M, Mattson 1VIP (2004) Cell cycle activation linked to neuronal cell death initiated by DNA damage. Neuron 41: 549-561
18. Silva A R, Santos A C, Farfel J M, Grinberg L T, Ferretti R E, Campos A H, Cunha I W, Begnami M D, Rocha R M, Carraro D M, de Braganca Pereira C A, Jacob-Filho W, Brentani H (2014) Repair of oxidative DNA damage, cell-cycle regulation and neuronal death may influence the clinical manifestation of Alzheimer's disease. PloS one 9: e99897 doi:10.1371/j ournal-.pone.0099897
19. Simpson J E, Ince P G, Matthews F E, Shaw P J, Heath P R, Brayne C, Garwood C, Higginbottom A, Wharton S B, Function MRCC, Ageing Neuropathology Study G (2015) A neuronal DNA damage response is detected at the earliest stages of Alzheimer's neuropathology and correlates with cognitive impairment in the Medical Research Council's Cognitive Function and Ageing Study ageing brain cohort. Neuropathol Appl Neurobiol 41: 483-496 doi:10.1111/nan.12202
20. Nishimura M, Tomimoto H, Suenaga T, Namba Y, Ikeda K, Akiguchi I, Kimura J (1995) Immunocytochemical characterization of glial fibrillary tangles in Alzheimer's disease brain. The American journal of pathology 146: 1052-1058
21. Ferrer I, Lopez-Gonzalez I, Carmona M, Arregui L, Dalfo E, Torrejon-Escribano B, Diehl R, Kovacs G G (2014) Glial and neuronal tau pathology in tauopathies: characterization of disease-specific phenotypes and tau pathology progression. J Neuropathol Exp Neurol 73: 81-97 doi:10.1097/NEN.0000000000000030
22. Arai T, Ikeda K, Akiyama H, Shikamoto Y, Tsuchiya K, Yagishita S, Beach T, Rogers J, Schwab C, McGeer P L (2001) Distinct isoforms of tau aggregated in neurons and glial cells in brains of patients with Pick's disease, corticobasal degeneration and progressive supranuclear palsy. Acta Neuropathol 101: 167-173
23. Harada A, Oguchi K, Okabe S, Kuno J, Terada S, Ohshima T, Sato-Yoshitake R, Takei Y, Noda T, Hirokawa N (1994) Altered microtubule organization in small-calibre axons of mice lacking tau protein. Nature 369: 488-491 doi:10.1038/369488a0
24. Mandelkow E, Mandelkow E M (1995) Microtubules and microtubule-associated proteins. Current opinion in cell biology 7: 72-81

Example 2. MAPT (Tau) Expression is a Biomarker for an Increased Rate of Survival in Pediatric Neuroblastoma Although the impact of MAPT (Tau) expression has been well documented for neuronal cells in the context of tauopathies and neurodegenerative diseases, the impact and role of Tau expression in cancer, and specifically cancers of neuronal origin, is in its infancy. To determine the correlation between MAPT expression and survival in pediatric neuroblastoma, MAPT gene expression for samples from the TARGET pediatric neuroblastoma dataset was assessed. Initial analyses indicated that increased MAPT expression correlated with increased overall survival in neuroblastoma but not in ovarian cancer. Expression of apoptosis- and proliferation-effector genes in the neuroblastoma samples was consistent with the MAPT related survival result. Furthermore, higher neuroblastoma expression of APP was also associated with neurodegeneration, correlated with better neuroblastoma survival rates. Gene expression associated with neuronal degenerative diseases was associated with a better neuroblastoma outcome.

BACKGROUND

Expression of the Tau protein, encoded by the MAPT gene (Microtubule Associated Protein—Tau), is associated with several neurodegenerative disorders that result in neuronal cell death[1,2]. The majority of research into the function of the Tau protein is driven by the context of tauopathies. There has been relatively little research investigating the role of Tau in cancer, particularly in cancers of neuronal origin.

Neuroblastoma is an aggressive pediatric cancer of neuronal origin that causes approximately 13% of all pediatric cancer deaths and is the primary cause of cancer-related death for children between the ages of one and five years[3]. It is the third most common pediatric cancer, after leukemia and brain cancers[4]. Furthermore, neuroblastoma tumors are able to mature spontaneously, and there are certain phenotypes, dubbed "ultra-high risk" that tend to have increased resistance to therapy[5-7]. The International Neuroblastoma Risk Group classification system[8] was developed to aid in the clinical management of pediatric neuroblastoma. Based on molecular and clinical features, patients are grouped into either low, intermediate, or high risk groups, with high risk groups having poor survival outcomes. Thus, there is a need to identify biological characteristics that may help better inform clinicians regarding the risk-status of the neuroblastoma patients[5]. In this example, the connection between Tau expression in neuroblastoma and survival rates was investigated.

2. Methods 2.1 MAPT, SNCA, APP, TARDBP, Apoptosis-Effector Gene and Pro Proliferative Gene Microarray and RNAseq Analysis.

Microarray and RNASeq values for MAPT were downloaded from cBioPortal.org. Also, microarray values for SNCA, APP, TARDBP, and a previously studied panel of apoptosis- and proliferation-effector genes[9], were downloaded from cBioPortal.org. Pearson correlation coefficients were obtained using Graphpad Prism software version 7.0. Only Pediatric neuroblastoma barcodes with either microarray or RNAseq data available, as indicated in Results, were used in this report.

2.2 Kaplan-Meier Analyses and Microarray Data

Clinical data, including overall survival data, for TARGET Pediatric Neuroblastoma and TCGA Provisional Ovarian Serous Cystadenocarcinoma (OV) were downloaded from cBioPortal.org. The barcodes (patients identifiers) representing 249 TARGET pediatric neuroblastoma samples with microarray data, 143 TARGET pediatric neuroblastoma samples with RNAseq data, and 558 TCGA provisional OV (ovarian cancer) samples with available microarray data were sorted from high to low based on the respective gene expression values (microarray or RNAseq). Next, overall survival relationships were obtained by matching gene expression data with survival data as indicated in Results. The overall survival data were then processed using Graphpad Prism software version 7.0, to generate Kaplan-Meier (KM) survival curves and to assess median survivals for each cohort tested.

2.3 MYCN Amplification Analysis

Amplification data for the MYCN gene for TARGET Pediatric Neuroblastoma barcodes with available microarray data (n=249) were downloaded from cBioPortal.org. Amplification data were then matched onto barcode microarray data. A Student's t-test was conducted, using the Microsoft Excel function, to distinguish MYCN amplification data representing the top and bottom 20% of MAPT microarray values 2.4 Risk Group Analysis Risk group classifications for TARGET pediatric neuroblastoma barcodes with available microarray data (n=249) were obtained from cBioPortal.org. Barcodes were first stratified by risk designation and then matched to barcode microarray data. A Student's t-test was conducted to distinguish MAPT expression levels among the high risk cohort representing the top 20% of the MAPT microarray values and all remaining, high risk barcodes (bottom 80%). Barcodes were then matched to overall survival data and KM analyses were conducted.

2.5 Analysis of MAPT, APP, and TARDBP Using the R2 Genomics Analysis and Visualization Platform.

Overall survival data and gene expression data for additional, independent neuroblastoma datasets were assessed using the 'R2: Genomics Analysis and Visualization Platform (http://r2.amc.nl)'. Survival distinctions based on MAPT expression were assessed using the Kaplan scan analysis tool as indicated in the Results section. The cutoff used for overall survival comparison was Median MAPT mRNA expression across the indicated dataset. Kaplan-Meier overall survival curves were generated using the R2 algorithm to compare survival outcomes between the top half and bottom half of MAPT expressers in each indicated dataset.

3. RESULTS 3.1 MAPT (Tau) Expression and Survival Rates

To determine whether Tau expression may confer a survival advantage in pediatric neuroblastoma, the rate of overall survival was compared for patients representing the top and bottom quintiles (20%) of MAPT expressers, based on MAPT microarray values obtained from cBioPortal.org. The microarray values, including averages, for the top and bottom 20% levels of expression, respectively, for MAPT for pediatric neuroblastoma were examined. Results indicated that the higher MAPT microarray values were associated with a significantly increased overall survival rate in pediatric neuroblastoma (FIG. 6A). The median survival periods and p-values for the log-rank tests are given in the legend for FIG. 6.

To determine whether this association of increased MAPT microarray levels with increased overall survival rates was specific to pediatric neuroblastoma, overall survival data for the OV dataset from cBioPortal.org was downloaded, and the microarray and KM analyses were conducted. Results indicated that for the OV dataset, MAPT expression levels were not associated with distinct overall survival advantages (FIG. 6B).

To determine whether the increased survival advantage in high MAPT-expressing pediatric neuroblastoma patients was specific for Tau, it was assessed whether there was a survival advantage conferred by alpha-synuclein (SNCA), using the microarray expression values in pediatric neuroblastoma patients from the same cohort as was used for the MAPT microarray analysis. Results indicated that there were no significant overall survival differences represented by the pediatric neuroblastoma barcodes for the top and bottom SNCA expression quintiles (FIG. 6C).

To further verify the initial results of MAPT microarray values associating with a survival advantage in pediatric neuroblastoma, the analysis was repeated using RNAseq values obtained from cBioPortal.org and compared the top 50% and 20% of MAPT expressers with their corresponding lower level MAPT expressers (bottom 50% and bottom 20%, respectively) for overall survival. In both cases, the initial result was supported, and the same trend towards increased survival in high MAPT was observed (FIG. 6D, 6E). Because there was a higher sample size of barcodes with microarray data available (n=249) than RNAseq data available (n=143), the microarray values were used for the remaining analyses in this report.

3.2 Pediatric Neuroblastoma Apoptosis-Effector Gene Microarray Values Correlated with MAPT Microarray Values Because Tau is associated with neurodegenerative disease and neuronal cell death, it was determined whether apoptosis-effector genes were expressed at higher levels in the neuroblastoma samples represented by the barcodes with higher levels of MAPT microarray values. A set of 28 apoptosis effector genes[9] was first evaluated for microarray expression in the same cohort of pediatric neuroblastoma barcodes which were used for the previous KM analyses. Of those 28 genes, a subset of seven apoptosis-effector genes was identified that have significantly increased microarray values associated with barcodes that represented the top 20% of MAPT expressers when compared to the bottom 20% of MAPT expressers: AIFM2, CASP3, CASP9, COX6A1, CRADD, and GZMB (Table 7).

To verify the above positive correlations of apoptosis-effector gene microarray values with MAPT microarray values, the Pearson correlation coefficients were obtained for the MAPT expression levels and the expression levels of AIFM2, CASP3, CASP9, COX6A1, CRADD, and GZMB in pediatric neuroblastoma. In each case, there was a statistically significant positive correlation with MAPT expression (FIG. 7).

Figures 8A, 8B:
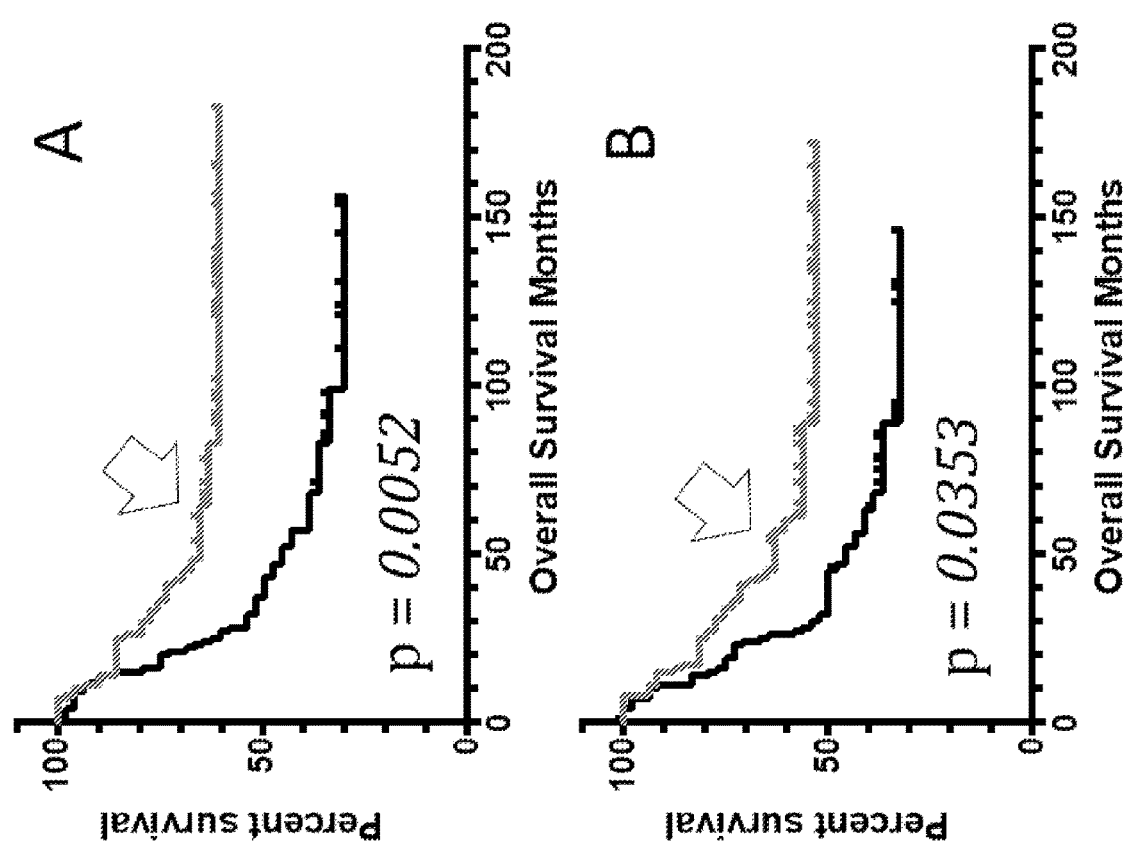
FIGS. 8A and 8B. Kaplan-Meier curves representing distinct apoptosis-effector gene expression levels.

To determine whether any of the seven above identified apoptosis-effector genes could represent independent markers of survival rates, the overall survival data for pediatric neuroblastoma barcodes representing the top quintile (20%) and bottom quintile (20%) of AIFM2, CASP3, CASP9, COX6A1, CRADD, and GZMB expression levels were obtained for KM analysis, using the same method as indicated previously. Results indicated that both CASP3 and CASP9, two critical components of apoptosis functionality, represented independent markers of survival, with barcodes representing the highest 20% of both CASP3 and CASP9 having significantly increased survival rates (FIG. 8).

3.3 Pediatric Neuroblastoma Proliferation-Effector Gene Microarray Values Inversely Correlated with MAPT Microarray Values It was next determined whether low levels of MAPT expression were associated with increased proliferation-effector gene expression. A set of 11 histone genes[9] was first evaluated for microarray expression in the same cohort of pediatric neuroblastoma barcodes with microarray data available and used for the previous KM and apoptosis analyses. Of the 11 histone genes, 10 genes were identified that had increased microarray values statistically, significantly associated with barcodes that represented the bottom 20% of MAPT expressers (when compared to the top 20% of MAPT expressers): H1FX, H2AFX, HIST1H2AL, HIST1H2BK, HIST1H3J, HIST1H4B, HIST1H4J, HIST2H2BE, HIST2H3D, and HIST3H2A (Table 8). Only H3F3B expression represented the opposite trend, with the top quintile of MAPT expressers also expressing increased H3F3B (Table 8).

To verify the above inverse correlations of proliferation-effector gene microarray values with MAPT microarray values, the Pearson correlation coefficients were obtained for the MAPT expression levels and the expression levels of H1FX, H2AFX, H3F3B, HIST1H2AL, HIST1H2BK, HIST1H3J, HIST1H4B, HIST1H4J, HIST2H2BE, HIST2H3D, and HIST3H2A in pediatric neuroblastoma. In all cases, except for H3F3B, there was a statistically significant inverse correlation with MAPT expression (FIG. 9).

Figures 10A, 10B:
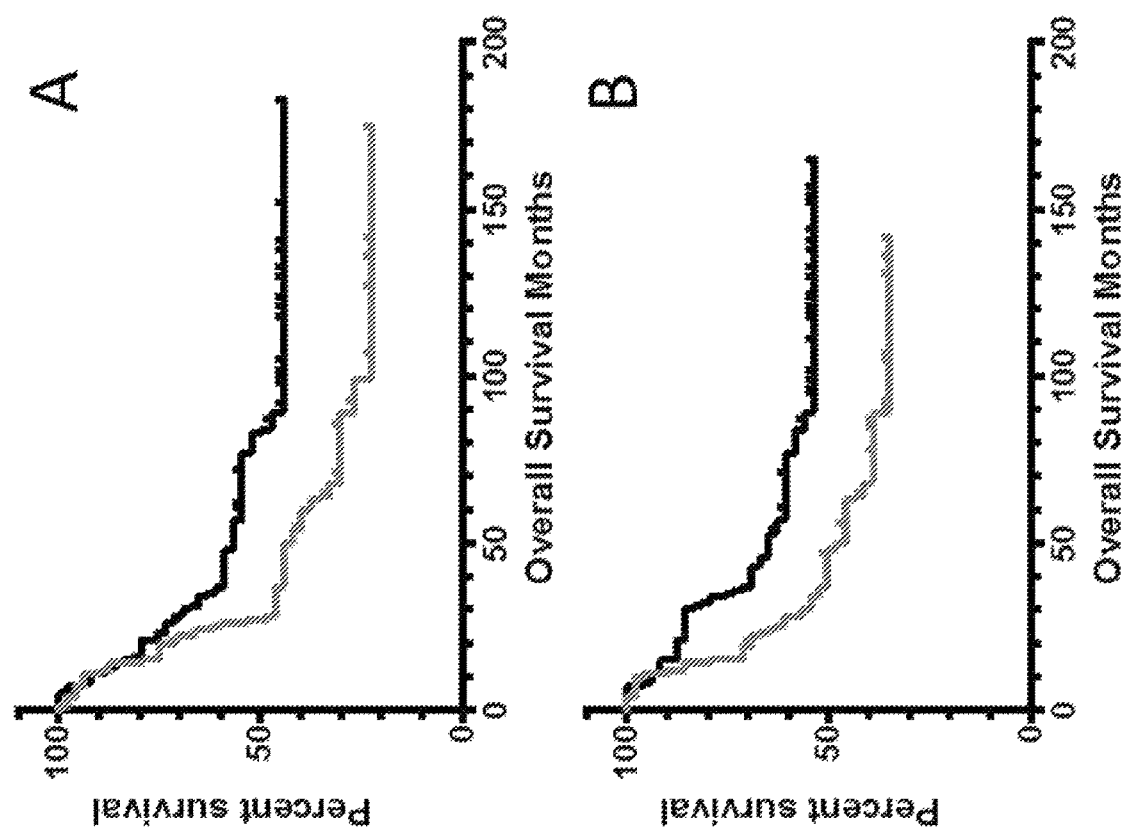
FIGS. 10A and 10B. Kaplan-Meier curves representing distinct proliferation-effector gene expression levels.

To determine whether the expression of any of the above histone genes could represent an independent marker for survival rates, the overall survival data for pediatric neuroblastoma barcodes representing the top quintile (20%) and bottom quintile (20%) for H1FX, H2AFX, HIST1H2AL, HIST1H2BK, HIST1H3J, HIST1H4B, HIST1H4J, HIST2H2BE, HIST2H3D, and HIST3H2A expression levels were obtained for KM analysis. Results indicated that both H1FX and HIST2H3D represented independent markers of survival, with barcodes representing the highest 20% of both H1FX and HIST2H3D having significantly decreased survival rates (FIG. 10).

3.4 MYCN Amplification Correlated with MAPT Microarray Values

It was next determined whether MAPT expression could be correlated with other risk factors for pediatric neuroblastoma. Amplification of MYCN is classically associated with neuroblastoma, and neuroblastoma patients with MYCN amplifications have worse outcomes[10-12]. As such, it was next determined whether MAPT expression correlated with MYCN amplification. MYCN amplification was compared between the top quintile of MAPT expressers and bottom quintile of MAPT expressers. It was determined that the bottom quintile of MAPT-expressing barcodes, that also had decreased overall survival, also had a significantly greater incidence of MYCN amplification (Table 9). There were no barcodes in the top quintile of MAPT expressers that had an MYCN amplification.

3.5 Risk Group Correlated with MAPT Microarray Values

Figure 11:
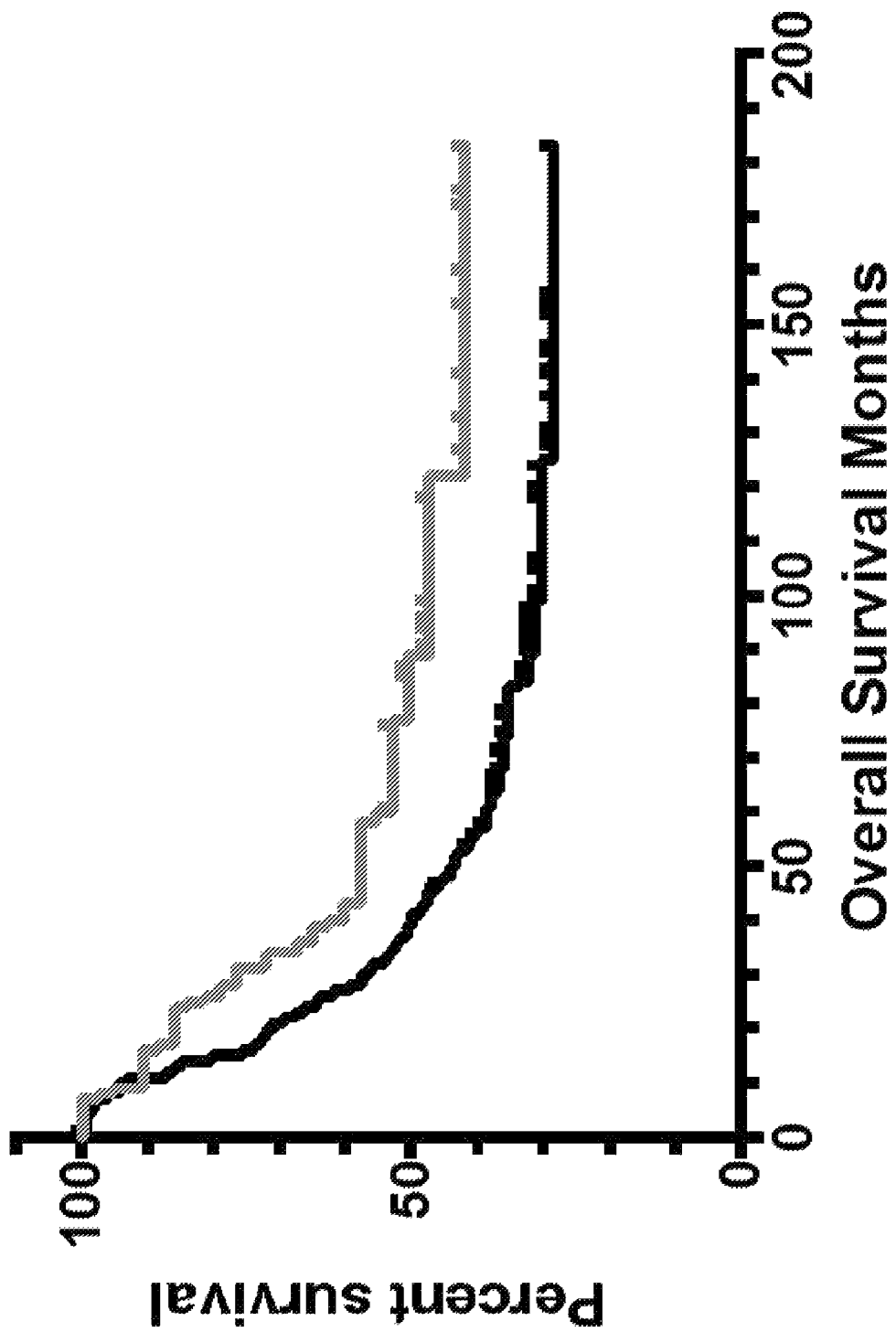
FIG. 11. Kaplan-Meier curves representing distinct MAPT gene expression levels among the high risk cohort of pediatric neuroblastoma barcodes. (A) KM OS curve for high risk pediatric neuroblastoma barcode microarray values in the top quintile (20%) of MAPT expressers (n=43, gray), compared to the OS for all remaining barcodes, which represents the bottom 80% of MAPT expressers (n=174, black). Mean OS for the top quintile of high risk MAPT expressers, 89 months; mean OS for all remaining barcodes (bottom 80%) of high risk MAPT expressers, 39 months. Log rank comparison p-value=0.0440.

Given that pediatric neuroblastoma is grouped into three risk categories (high, intermediate, and low) based on clinical and molecular characteristics of patients, it was determined whether MAPT expression could be a biomarker for the high risk patients. The barcodes used in the previous analyses were stratified by risk group based on risk group distinction available in the original TARGET dataset. It was next established that there was a statistically significant difference in MAPT expression between the top 20% and all remaining (bottom 80%) barcodes, solely among the high risk cohort of the barcodes (FIG. 11). Finally, a KM analysis was performed on pediatric neuroblastoma barcodes representing the top quintile of MAPT expressers and the bottom 80% of MAPT expressers. Results indicated that the high risk barcodes representing the top quintile of MAPT expressers (FIG. 11) had significantly increased survival rates when compared to all remaining high risk barcodes (FIG. 11). (The median survival periods and p-values for the log-rank tests are given in the legend for FIG. 11.)

Figures 12A, 12B:
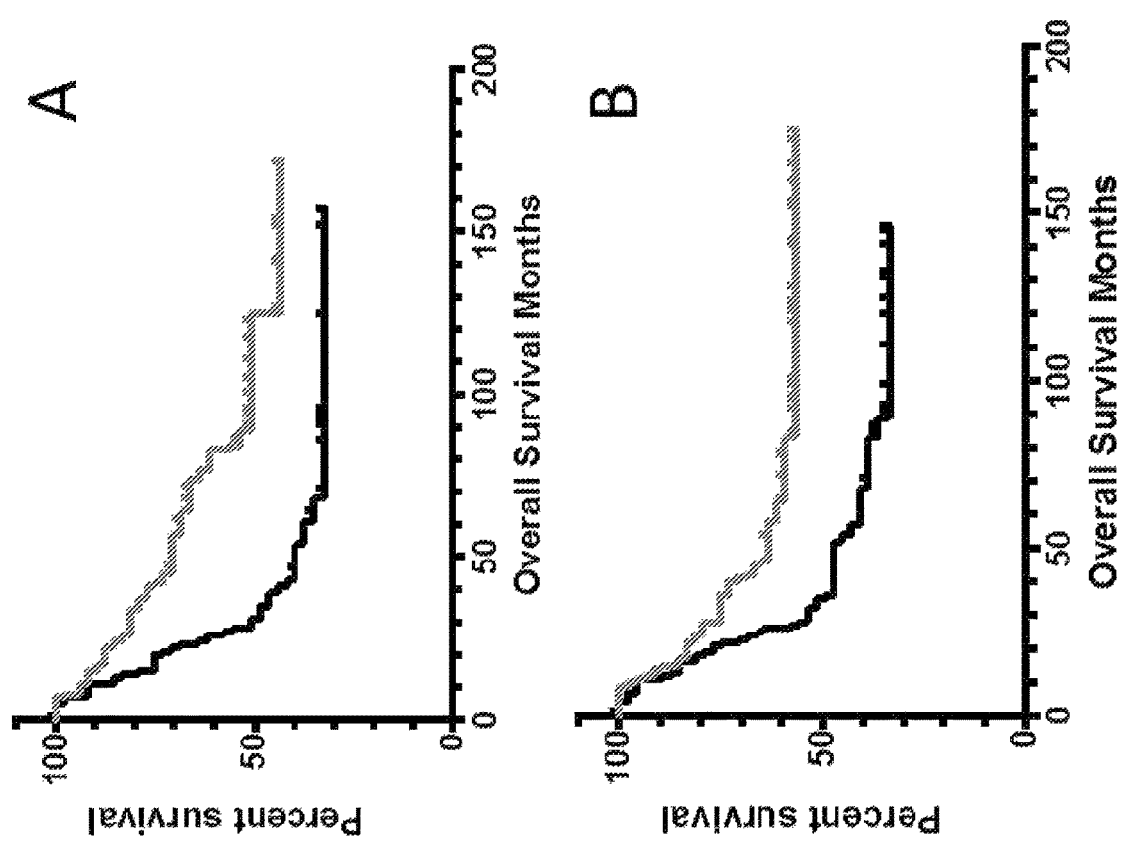
FIGS. 12A and 12B. Kaplan-Meier curves representing distinct APP and TARDBP gene expression levels.

3.6 APP (Amyloid Precursor Protein) and TARDBP (TAR DNA-Binding Protein 43) Expression and Survival Rates for Neuroblastoma To determine whether the increased survival advantage in high MAPT-expressing pediatric neuroblastoma patients could be observed for other neurotoxic proteins, it was assessed whether there was a survival advantage associated with high APP microarray expression values in pediatric neuroblastoma patients. Results indicated that higher APP microarray values were associated with a significantly increased overall survival rate in pediatric neuroblastoma (FIG. 12A).

It was next determined whether increased microarray expression values of TARDBP, the expression of which has been associated with dementia[13, 14] and Amyotrophic Lateral Sclerosis (ALS)[15], correlates with a survival advantage for the pediatric neuroblastoma patients. The microarray values, including averages, for the top and bottom 20% levels of expression, respectively, for TARDBP for pediatric neuroblastoma are provided in the SOM. (These microarray value averages represented statistically significant differences.) Results indicated that the higher TARDBP microarray values were associated with a significantly increased overall survival rate in pediatric neuroblastoma (FIG. 12B). The median survival periods and p-values for the log-rank tests for both APP and TARDBP expression are given in the figure legend for FIG. 12.

3.7 Analysis of Survival Associations with MAPT, APP, and TARDBP Expression in Additional Neuroblastoma Datasets from the R2: Genomics Analysis and Visualization Platform.

Figure 13:
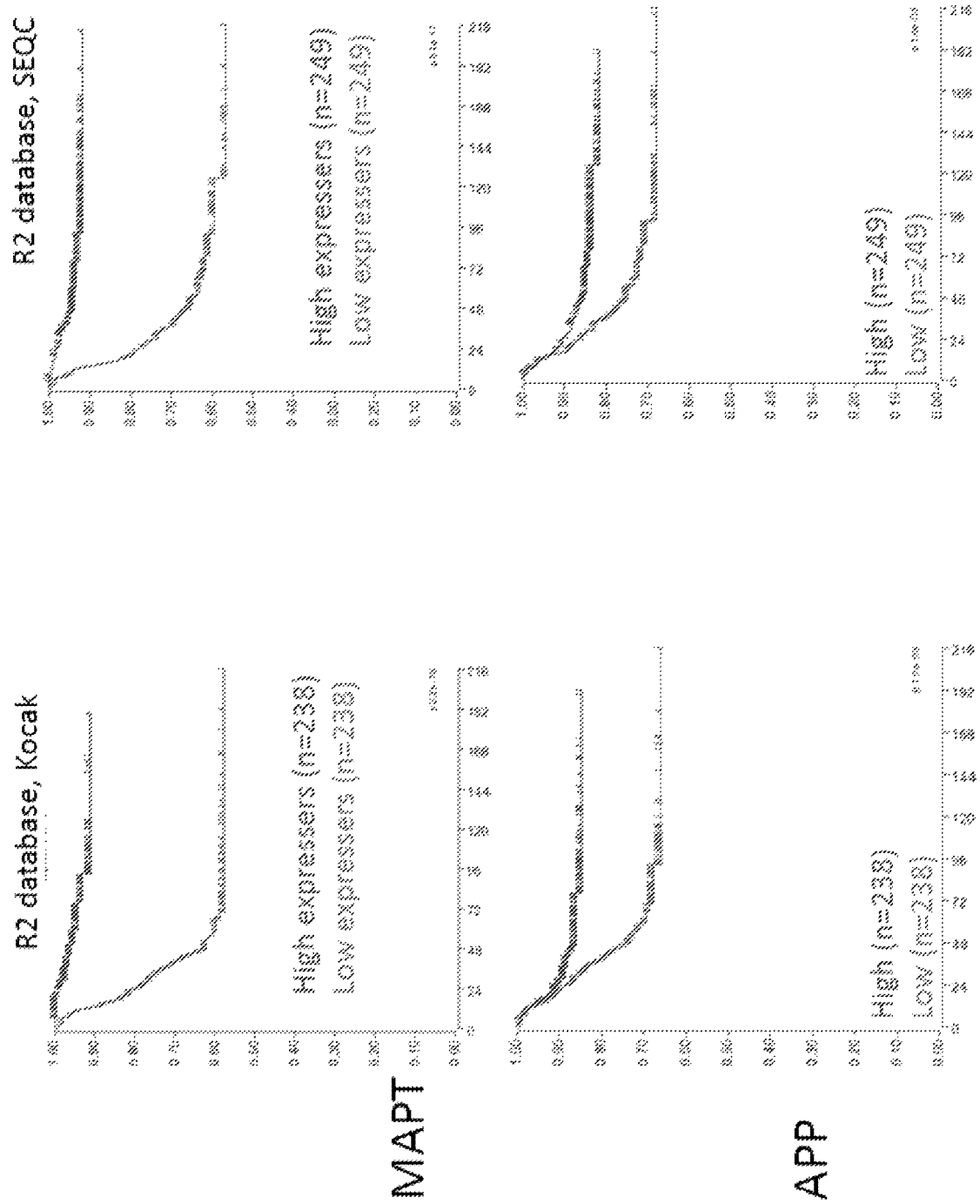
FIG. 13. Kaplan-Meier analyses for two additional neuroblastoma datasets for high and low MAPT and APP expressers. p-values in lower right corners of KM plots.

To determine whether MAPT mRNA expression is associated with improved survival outcomes in additional, independent neuroblastoma datasets, the R2: Genomics analysis and visualization platform was used. Two additional neuroblastoma datasets were analyzed, with results indicating a strong, statistically significant association of MAPT expression with longer survival (FIG. 13). Also, the two replicative datasets were consistent with the above results for APP expression, which indicated that a higher level of APP was associated with a higher rate of survival. However, these two R2-based datasets were not consistent with above results for TARDBP and did not replicate the association of high TARDBP expression levels with longer survival.

4. DISCUSSION

Although the overall survival rates for pediatric neuroblastoma have been steadily increasing from 53% between 1975-1977 to 74% between 2005-2011, investigating the molecular basis for neuroblastoma will continue to improve patient outcomes[16]. The above results indicated that high MAPT expression correlated with better survival for pediatric neuroblastoma, and including in the subset of the high-risk cohort of patients. While the MAPT expression differences studied here can seem as modest distinctions, despite tests for statistical significance that indicate otherwise, the differences likely represent the expression gradient realities[17, 18] of a natural cellular and tissue context, rather than an experimental "on/off" construction. In any event, the distinction of expression levels between quintiles, for MAPT, was also supported by correlation plots representing the entire MAPT expression dataset, as well as with two additional, replicative datasets.

The result that higher MAPT expression correlates with better outcomes was consistent with higher expression of certain apoptosis-effector genes among the samples represented by the high MAPT expression. Likewise, the result was consistent with the lower expression of the pro-proliferative histone genes among the samples that had a high MAPT expression. Importantly, the expression of MAPT, the apoptosis effector genes, and the histone genes could all be used as independent biomarkers of survival distinctions. Finally, consistent with the neuronal degradation impact of increased expression of MAPT, well known in neurodegenerative conditions, the overexpression of the APP gene also correlated with better survival rates for pediatric neuroblastoma, for all three datasets, i.e., the cBioPortal.org dataset and the R2 datasets.

There were TARGET microarray data for 249 patients and RNAseq data available for 143 patients. Thus, this analyses only incorporated the subset of the total TARGET pediatric neuroblastoma dataset (n=1076) that had gene expression data available. Regardless, when the bottom quintile of MAPT expressers (n=49) used in the analyses was compared to all remaining barcodes in the population of barcodes in the TARGET pediatric neuroblastoma dataset the result is consistent with the results presented in this report. The bottom quintile of MAPT expressers used in the analyses has a statistically significant worse survival outcome than all remaining barcodes in the pediatric neuroblastoma population in the TARGET pediatric neuroblastoma dataset (n=1027, p<0.0001).

There have been previous studies conducted assessing Tau in neuroblastoma cell lines[19-22]. For example, Monroy-Ramirez et al. found that overexpression of the Tau protein causes significant deformity in nuclear architecture in a neuroblastoma cell line (SH-SY5Y)[23]. However, the majority of these previous reports investigated Tau in the context of Alzheimer's and tauopathies, often using neuroblastoma cell lines as a surrogate for neural cells. That is, the role of Tau in the development of neurological cancers has not been investigated. Cancer research, and treatment relating to Tau has focused on cancers of non-neurological origin where Tau has been a target because of its role as a microtubule stabilizer. For example, Tau downregulation has been demonstrated to increase sensitivity to taxane in breast cancer cells[24].

Caspase-3 is the primary caspase associated with neural cell death in Alzheimer's disease cleavage of the amyloid-beta 4A precursor protein[25]. Caspase-3 cleaves the APP family members (including APLP1 and APLP2), generating a C-terminal peptide that contributes to neurotoxicity[26]. Consistent with the results in APP, the top quintile of APLP2 expressers had increased overall survival when compared to the bottom quintile of APLP2 expressers in the TARGET pediatric neuroblastoma dataset (unpublished observations).

Microtubule-stabilizing agents are widely used in cancer treatment, including paclitaxel, whose mechanism of microtubule stabilization was first elucidated in the late 1970s[27]; with clinical trials following thereafter[28]. Bouge and colleagues have demonstrated in a *Drosophila* model that an excess expression of human Tau protein induces mitotic arrest, which leads to aneuploidy and cell death[32]. Moreover, a MAPT-EGF fusion protein has demonstrated a proliferation-dependent cytotoxicity and the ability to inhibit mitosis in EGFR-overexpressing HEK293 kidney cancer cells through the stabilization of microtubules[33]. Tau function being analogous to paclitaxel activity, and causing an anti-mitotic effect, may lie at the heart of an explanation for the negative correlation between MAPT expression and proliferation-effector gene expression.

Importantly, the above results inform ongoing clinical trials. Fenretinide is currently being studied in clinical trials for neuroblastoma (clinicaltrials.gov). Fenretinide causes the buildup of ceramides in tumor cells[34] It also has been established that ceramides are key mediators of neuronal apoptosis in Alzheimer's disease[35]. Moreover, in vitro cell culture work suggests that sphingolipids, including ceramides, may cause or accelerate APP and MAPT-mediated pathology[36] These data, coupled with the above results, provide that Fenretinide could facilitate MAPT- and APP-mediated cell death in neuroblastoma, particularly in patients where MAPT expression is low prior to treatment.

TABLE 7

Average microarray values for pediatric neuroblastoma barcodes representing high and low expression of MAPT

| Apoptosis Effector Gene | Bottom 20% MAPT Microarray Values | Top 20% MAPT Microarray Values | p-value |
|---|---|---|---|
| AIFM2 | 6.06 | 6.32 | <0.0001 |
| BAD | 7.46 | 7.65 | 0.0004 |
| CASP3 | 7.61 | 7.86 | 0.0101 |
| CASP9 | 6.63 | 7.12 | <0.0001 |
| COX6A1 | 9.24 | 9.54 | 0.0023 |
| CRADD | 6.58 | 6.78 | 0.0018 |
| GZMB | 5.86 | 6.37 | 0.006 |

TABLE 8

Average microarray values for pediatric neuroblastoma barcodes representing high and low expression of MAPT

| Histone Proliferation Effector Gene | Bottom 20% MAPT Microarray Values | Top 20% MAPT Microarray Values | p-value |
|---|---|---|---|
| H1FX | 8.37 | 8.18 | 0.0147 |
| H2AFX | 7.75 | 7.48 | 0.0002 |
| H3F3B | 10.19 | 10.45 | 0.01 |
| HIST1H2AL | 7.59 | 6.86 | <0.0001 |
| HIST1H2BK | 6.12 | 5.57 | <0.0001 |
| HIST1H3J | 7.71 | 6.83 | <0.0001 |
| HIST1H4B | 10.38 | 9.74 | 0.0001 |
| HIST1H4J | 8.10 | 7.89 | 0.0214 |
| HIST2H2BE | 9.00 | 8.69 | 0.0204 |
| HIST2H3D | 10.09 | 8.96 | <0.0001 |
| HIST3H2A | 8.75 | 8.46 | 0.0479 |

TABLE 9

Identifying MYCN copy number variation associations with MAPT expression

| | Bottom Quintile MAPT Expressers | Top Quintile MAPT Expressers | p-value |
|---|---|---|---|
| Percent of barcodes with MYCN amplification | 0.53 | 0.00 | <0.0001 |

Abbreviations

ALS, Amyotrophic Lateral Sclerosis; APP, Amyloid Precursor Protein gene; CASP3, Caspase 3 gene; CASP9, Caspase 9 gene; H2AFX, H2A histone family, member X gene; HIST1H2AL, Histone H2A type 1 gene; HIST1H2BK, Histone H2B type 1-K gene; HIST1H3J, Histone H3J gene; HIST1H4B, Histone H4B gene; HIST2H2BE, Histone H2B type 2-E gene; HUGO, human genome organization; KM, Kaplan-Meier survival curve; MAPT, Tau gene; OV, Ovarian cancer; SNCA, alpha-synuclein gene; TARDBP, Transactive response DNA binding protein 43 kDa; TCGA, the cancer genome atlas.

REFERENCES CITED IN THIS EXAMPLE

1. Spillantini M G, Goedert M. Tau pathology and neurodegeneration. Lancet Neurol 2013; 12:609-22.
2. Buee L, Troquier L, Burnouf S, Belarbi K, Van der Jeugd A, Ahmed T, Fernandez-Gomez F, Caillierez R, Grosjean M E, Begard S, et al. From tau phosphorylation to tau aggregation: what about neuronal death? Biochemical Society transactions 2010; 38:967-72.
3. Louis C U, Shohet J M. Neuroblastoma: molecular pathogenesis and therapy. Annu Rev Med 2015; 66:49-63.
4. Maris J M, Hogarty M D, Bagatell R, Cohn S L. Neuroblastoma. Lancet 2007; 369:2106-20.
5. Davidoff A M. Neuroblastoma. Semin Pediatr Surg 2012; 21:2-14.
6. Russo R, Cimmino F, Pezone L, Manna F, Avitabile M, Langella C, Koster J, Casale F, Raia M, Viola G, et al. Kinome expression profiling of human neuroblastoma tumors identifies potential drug targets for ultra high-risk patients. Carcinogenesis 2017; 38:1011-20.
7. Saarinen-Pihkala U M, Jahnukainen K, Wikstrom S, Koivusalo A, Karikoski R, Sariola H, Hovi L. Ultra-high-risk group within the high-risk neuroblastoma category. J Pediatr Hematol Oncol 2013; 35:e254-9.
8. Cohn S L, Pearson A D, London W B, Monclair T, Ambros P F, Brodeur G M, Faldum A, Hero B, Iehara T, Machin D, et al. The International Neuroblastoma Risk Group (INRG) classification system: an INRG Task Force report. Journal of clinical oncology: official journal of the American Society of Clinical Oncology 2009; 27:289-97.
9. Mauro J A, Blanck G. Functionally distinct gene classes as bigger or smaller transcription factor traps: a possible stochastic component to sequential gene expression programs in cancer. Gene 2014; 536:398-406.
10. Cheng J M, Hiemstra J L, Schneider S S, Naumova A, Cheung N K, Cohn S L, Diller L, Sapienza C, Brodeur G M. Preferential amplification of the paternal allele of the N-myc gene in human neuroblastomas. Nature genetics 1993; 4:191-4.
11. Emanuel B S, Balaban G, Boyd J P, Grossman A, Negishi M, Parmiter A, Glick M C. N-myc amplification in multiple homogeneously staining regions in two human neuroblastomas. Proceedings of the National Academy of Sciences of the United States of America 1985; 82:3736-40.
12. Brodeur G M, Seeger R C, Schwab M, Varmus H E, Bishop J M. Amplification of N-myc in untreated human neuroblastomas correlates with advanced disease stage. Science 1984; 224:1121-4.
13. Borroni B, Bonvicini C, Alberici A, Buratti E, Agosti C, Archetti S, Papetti A, Stuani C, Di Luca M, Gennarelli M, et al. Mutation within TARDBP leads to frontotemporal dementia without motor neuron disease. Human mutation 2009; 30:E974-83.
14. Floris G, Borghero G, Cannas A, Di Stefano F, Murru M R, Corongiu D, Cuccu S, Tranquilli S, Cherchi M V, Serra A, et al. Clinical phenotypes and radiological findings in frontotemporal dementia related to TAR-DBP mutations. J Neurol 2015; 262:375-84.
15. Harms M M, Miller T M, Baloh R H. TARDBP-Related Amyotrophic Lateral Sclerosis. In: Adam M P, Ardinger H H, Pagon R A, Wallace S E, Bean L J H, Stephens K, Amemiya A, eds. GeneReviews(®). Seattle (Wash.), 1993.
16. Siegel R L, Miller K D, Jemal A. Cancer statistics, 2016. CA Cancer J Clin 2016; 66:7-30.
17. Ford S A, Blanck G. Signal persistence and amplification in cancer development and possible, related opportunities for novel therapies. Biochimica et biophysica acta 2014; 1855:18-23.
18. Kellogg R A, Tay S. Noise facilitates transcriptional control under dynamic inputs. Cell 2015; 160:381-92.

19. Lee Y J, Kim J E, Kwak M H, Go J, Yang S Y, Kwon H S, Kim B C, Kim J M, Hwang D Y. Selenium treatment significantly inhibits tumor necrosis factor-alpha-induced cell death and tau hyperphosphorylation in neuroblastoma cells. Mol Med Rep 2014; 10:1869-74.
20. Lee M, McGeer E, McGeer P L. Activated human microglia stimulate neuroblastoma cells to upregulate production of beta amyloid protein and tau: implications for Alzheimer's disease pathogenesis. Neurobiol Aging 2015; 36:42-52.
21. Petroni D, Tsai J, Agrawal K, Mondal D, George W. Low-dose methylmercury-induced oxidative stress, cytotoxicity, and tau-hyperphosphorylation in human neuroblastoma (SH-SY5Y) cells. Environ Toxicol 2012; 27:549-55.
22. Choi S, Oh J H, Kim H, Nam S H, Shin J, Park J S. Protective Effect of Tat PTD-Hsp27 Fusion Protein on Tau Hyperphosphorylation Induced by Okadaic Acid in the Human Neuroblastoma Cell Line SH-SY5Y. Cell Mol Neurobiol 2015; 35:1049-59.
23. Monroy-Ramirez H C, Basurto-Islas G, Mena R, Cisneros B, Binder L I, Avila J, Garcia-Sierra F. Alterations in the nuclear architecture produced by the overexpression of tau protein in neuroblastoma cells. J Alzheimers Dis 2013; 36:503-20.
24. Ikeda H, Taira N, Hara F, Fujita T, Yamamoto H, Soh J, Toyooka S, Nogami T, Shien T, Doihara H, et al. The estrogen receptor influences microtubule-associated protein tau (MAPT) expression and the selective estrogen receptor inhibitor fulvestrant downregulates MAPT and increases the sensitivity to taxane in breast cancer cells. Breast Cancer Res 2010; 12:R43.
25. Gervais F G, Xu D, Robertson G S, Vaillancourt J P, Zhu Y, Huang J, LeBlanc A, Smith D, Rigby M, Shearman M S, et al. Involvement of caspases in proteolytic cleavage of Alzheimer's amyloid-beta precursor protein and amyloidogenic A beta peptide formation. Cell 1999; 97:395-406.
26. Galvan V, Chen S, Lu D, Logvinova A, Goldsmith P, Koo E H, Bredesen D E. Caspase cleavage of members of the amyloid precursor family of proteins. J Neurochem 2002; 82:283-94.
27. Schiff P B, Fant J, Horwitz S B. Promotion of microtubule assembly in vitro by taxol. Nature 1979; 277:665-7.
28. Wiernik P H, Schwartz E L, Strauman J J, Dutcher J P, Lipton R B, Paietta E. Phase I clinical and pharmacokinetic study of taxol. Cancer research 1987; 47:2486-93.
29. Samadi N, Bekele R T, Goping I S, Schang L M, Brindley D N. Lysophosphatidate induces chemo-resistance by releasing breast cancer cells from taxol-induced mitotic arrest. PloS one 2011; 6:e20608.
30. Snyder J P, Nettles J H, Cornett B, Downing K H, Nogales E. The binding conformation of Taxol in beta-tubulin: a model based on electron crystallographic density. Proceedings of the National Academy of Sciences of the United States of America 2001; 98:5312-6.
31. Arnal I, Wade R H. How does taxol stabilize microtubules? Current biology: CB 1995; 5:900-8.
32. Bouge A L, Parmentier M L. Tau excess impairs mitosis and kinesin-5 function, leading to aneuploidy and cell death. Dis Model Mech 2016; 9:307-19.
33. Akinrinmade O A, Jordaan S, Hristodorov D, Mladenov R, Mungra N, Chetty S, Barth S. Human MAP Tau Based Targeted Cytolytic Fusion Proteins. Biomedicines 2017; 5.
34. Wu J M, DiPietrantonio A M, Hsieh T C. Mechanism of fenretinide (4-HPR)-induced cell death. Apoptosis: an international journal on programmed cell death 2001; 6:377-88.
35. Jazvinscak Jembrek M, Hof P R, Simic G. Ceramides in Alzheimer's Disease: Key Mediators of Neuronal Apoptosis Induced by Oxidative Stress and Abeta Accumulation. Oxid Med Cell Longev 2015; 2015:346783.
36. Mielke M M, Haughey N J, Bandaru V V R, Zetterberg H, Blennow K, Andreasson U, Johnson S C, Gleason C E, Blazel H M, Puglielli L, et al. Cerebrospinal fluid sphingolipids, beta-amyloid, and tau in adults at risk for Alzheimer's disease. Neurobiol Aging 2014; 35:2486-94.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method of alleviating or relieving a selected subject having pediatric neuroblastoma, comprising:
   obtaining a neuroblastoma tumor sample derived from a subject having pediatric neuroblastoma;
   quantifying an expression level of one or more biomarkers that are associated with overall survival in pediatric neuroblastoma in the neuroblastoma tumor sample derived from the subject and a noncancerous control from the subject, wherein the biomarker comprises one or more of MAPT, CASP3, and CASP9;
   identifying the selected subject as having a shorter overall survival if the expression level of one or more of the biomarkers MAPT, CASP3, and CASP9 is lower in the neuroblastoma tumor sample derived from the subject compared to a reference selected from the noncancerous control or expression level at the highest quintile (20%) of the biomarker levels of a reference population of pediatric neuroblastoma patient samples; and
   administering to the selected subject a therapeutically effective amount of an activator of MAPT, an activator of CASP3, an activator of CASP9, or a combination thereof.

2. The method of claim 1, wherein the biomarker comprises MAPT.

3. The method of claim 1, wherein the biomarker comprises CASP3.

4. The method of claim 1, wherein the biomarker comprises CASP9.

5. The method of claim 1, wherein the quantifying is carried out by one or more analyses selected from Polymerase Chain Reaction, Real Time-Polymerase Chain Reaction, Real Time Reverse Transcriptase-Polymerase Chain Reaction, Real-time quantitative RT-PCR, Northern blot analysis, in situ hybridization, and probe array.

6. The method of claim 1, wherein the expression level at the highest quintile (20%) of the biomarker levels of a reference population of pediatric neuroblastoma patient samples in the quantifying step is obtained from an independent dataset of neuroblastoma patient samples.

7. The method of claim 1, further comprising administering an appropriate pediatric neuroblastoma therapy to the selected subject based on the prediction of the selected subject as having a shorter overall survival.

8. The method of claim 1, further comprising administering an appropriate pediatric neuroblastoma therapy to the selected subject based on the prediction of the selected subject as having an overall survival of 37 months or less.

9. The method of claim 1, wherein the activator of MAPT is cordycepin.

* * * * *